(12) United States Patent
Furutani et al.

(10) Patent No.: US 9,783,828 B2
(45) Date of Patent: Oct. 10, 2017

(54) RECOMBINANT CELL, AND METHOD FOR PRODUCING ISOPRENE

(71) Applicants: SEKISUI CHEMICAL CO., LTD., Osaka (JP); FRAUNHOFER-GESELLSCHAFT ZUR FORDERUNG DER ANGEWANDTEN FORSCHUNG E.V., Munich (DE)

(72) Inventors: Masahiro Furutani, Tokyo (JP); Akihiro Uenishi, Tsukuba (JP); Koichiro Iwasa, Tokyo (JP); Stefan Jennewein, Aachen (DE); Rainer Fischer, Aachen (DE)

(73) Assignees: SEKISUI CHEMICAL CO., LTD., Osaka (JP); FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/437,034

(22) PCT Filed: Oct. 22, 2013

(86) PCT No.: PCT/JP2013/078558
§ 371 (c)(1),
(2) Date: Apr. 20, 2015

(87) PCT Pub. No.: WO2014/065271
PCT Pub. Date: May 1, 2014

(65) Prior Publication Data
US 2015/0284742 A1    Oct. 8, 2015

(30) Foreign Application Priority Data

Oct. 23, 2012 (JP) ................................ 2012-233571
Jun. 25, 2013 (JP) ................................ 2013-132423

(51) Int. Cl.
| | |
|---|---|
| *C12P 5/02* | (2006.01) |
| *C12N 1/20* | (2006.01) |
| *C12N 15/00* | (2006.01) |
| *C07H 21/04* | (2006.01) |
| *C12P 5/00* | (2006.01) |
| *C12N 9/88* | (2006.01) |
| *C12N 9/02* | (2006.01) |

(52) U.S. Cl.
CPC ............ *C12P 5/007* (2013.01); *C12N 9/0008* (2013.01); *C12N 9/88* (2013.01); *C12Y 302/01* (2013.01); *C12Y 102/07004* (2013.01); *C12Y 102/99002* (2013.01); *C12Y 402/03027* (2013.01)

(58) Field of Classification Search
None
See application file for complete search history.

(56) References Cited

U.S. PATENT DOCUMENTS

| | | | |
|---|---|---|---|
| 2009/0191593 A1 | 7/2009 | Burk et al. | |
| 2010/0317077 A1 | 12/2010 | Gaddy et al. | |
| 2011/0059499 A1 | 3/2011 | Simpson et al. | |
| 2013/0045891 A1 | 2/2013 | Beck et al. | |

FOREIGN PATENT DOCUMENTS

| | | |
|---|---|---|
| JP | 2011-505841 | 3/2011 |
| JP | 2011-509691 | 3/2011 |
| JP | 2011-512869 | 4/2011 |
| JP | 2011-518564 | 6/2011 |
| JP | 2011/524933 | 9/2011 |
| JP | 2012-147682 | 8/2012 |
| WO | 2009/076676 | 6/2009 |
| WO | 2009/094485 | 7/2009 |
| WO | 2009/132220 | 10/2009 |
| WO | 2011/160081 | 12/2011 |
| WO | 2012/058494 | 3/2012 |
| WO | 2013/063528 | 5/2013 |

OTHER PUBLICATIONS

International Search Report dated Jan. 21, 2014 in International (PCT) Application No. PCT/JP2013/078558.
J. Yang et al., "Bio-Isoprene Production using Exogenous MVA Pathway and Isoprene Synthase in *Escherichia Coli*", Bioresource Technology, vol. 104, pp. 642-647, 2012.
Supplementary Partial European Search Report dated Feb. 19, 2016, issued in corresponding European Patent Application No. 13 84 8830.
Supplementary European Search Report dated May 20, 2016 issued in parallel European Patent Application No. 13 84 8830.
Yang et al., "Enhancing Production of Bio-Isoprene Using Hybrid MVA Pathway and Isoprene Synthase in *E. coli*", PLOS ONE, vol. 7, No. 4, 2012, pp. 1-7.
Köpke et al., "Clostridium Ijungdahlii represents a microbial production platform based on syngas", Proceeding of The National Academy of Sciences of The United States of America, vol. 107, No. 29, 2010, pp. 13087-13092.
English translation of International Preliminary Report on Patentability and Written Opinion dated May 7, 2015 in PCT/JP2013/078558.

*Primary Examiner* — Iqbal H Chowdhury
(74) *Attorney, Agent, or Firm* — Wenderoth Lind & Ponack, L.L.P.

(57) ABSTRACT

To provide a series of techniques capable of producing isoprene from syngas or the like.
Provided is a recombinant cell prepared by introducing a nucleic acid encoding isoprene synthase into a host cell having an isopentenyl diphosphate synthesis ability by a non-mevalonate pathway, wherein the nucleic acid is expressed in the host cell, and the recombinant cell is capable of producing isoprene from at least one C1 compound selected from the group consisting of carbon monoxide, carbon dioxide, formic acid, and methanol. As the host cell, a *Clostridium* bacterium or a *Moorella* bacterium is exemplified. Also provided is a method for producing isoprene using the recombinant cell.

17 Claims, 4 Drawing Sheets

RECOMBINANT CELL, AND METHOD FOR PRODUCING ISOPRENE

TECHNICAL FIELD

The present invention relates to a recombinant cell capable of producing isoprene from a specific C1 compound such as carbon monoxide, and a method for producing isoprene using the recombinant cell.

BACKGROUND ART

Isoprene is a monomer raw material for synthetic polyisoprene, and is an important material, in particular, in the tire industry. In recent years, the technique for conversion from a production process of basic chemicals relying on petroleum to a production process from renewable resources such as plant resources has been developed and practical realization thereof is steadily progressing. Also regarding isoprene, for example, a production technique from saccharides as a raw material by recombinant *Escherichia coli* is known (Patent Documents 1 and 2).

Regarding the production process from renewable resources, most of the conventional techniques are production methods by microorganisms relying on organic substances, in particular, saccharides, glycerol or oil components, including the aforementioned isoprene production technique. However, for covering the global production quantity of a large number of basic chemicals derived from petroleum, the quantities of saccharides, glycerin and oil components derived from plant resources and the like that are currently available will be necessarily insufficient for carbon sources of microorganisms. In other words, the production quantity of basic chemicals by microorganisms relying on saccharides or oil components is limited also in the future. These processes also have a fear of competition with foods.

Syngas (synthesis gas) is a mixed gas mainly containing carbon monoxide, carbon dioxide, and hydrogen, which is efficiently obtained from waste, natural gas and coal by action of a metal catalyst under high temperature and high pressure. In the field of C1 chemistry by metal catalysts starting from syngas, a process for mass production of liquid chemicals such as methanol, formic acid and formaldehyde at low costs has been developed.

Carbon monoxide, carbon dioxide and hydrogen are contained in syngas derived from waste, industrial exhaust gas, natural gas or syngas derived from coal, and are available almost permanently. However, at present, examples of producing chemicals by microorganisms from C1 carbon sources represented by syngas are very limited. Only production of ethanol, 2,3-butanediol or the like from syngas is currently under development. In particular, there is little report about utilization of a syngas utilizing substance by a recombinant. Patent Document 3 discloses a production technique of isopropanol by a recombinant of *Escherichia coli*. In this technique, a plurality of CO metabolic enzyme genes are introduced into *Escherichia coli* to impart a syngas utilizing ability, and isopropanol is produced from syngas. However, this technique does not relate to production of isoprene.

PATENT DOCUMENT

Patent Document 1: JP 2011-505841 A
Patent Document 2: JP 2011-518564 A
Patent Document 3: JP 2011-509691 A

DISCLOSURE OF INVENTION

Technical Problem

In light of the above, an object of the present invention is to provide a series of techniques capable of producing isoprene from syngas or the like.

Solutions to Problem

One aspect of the present invention for solving the aforementioned problem is a recombinant cell prepared by introducing a nucleic acid encoding isoprene synthase into a host cell having an isopentenyl diphosphate synthesis ability by a non-mevalonate pathway, wherein the nucleic acid is expressed in the host cell, and the recombinant cell is capable of producing isoprene from at least one C1 compound selected from the group consisting of carbon monoxide, carbon dioxide, formic acid, and methanol.

The present invention relates to a recombinant cell capable of producing isoprene. The recombinant cell of the present invention is prepared by introducing a nucleic acid encoding isoprene synthase into a host cell having an "isopentenyl diphosphate synthesis ability by a non-mevalonate pathway", and the nucleic acid is expressed in the host cell. The recombinant cell is capable of producing isoprene from at least one C1 compound selected from the group consisting of carbon monoxide, carbon dioxide, formic acid, and methanol. According to the recombinant cell of the present invention, it is possible to synthesize isopentenyl diphosphate (IPP) from the C1 compound, and further to convert the synthesized IDD to isoprene. As a result, it is possible to produce isoprene from the C1 compound. By using the recombinant cell of the present invention, it is possible to produce isoprene, for example, from syngas containing carbon monoxide and/or carbon dioxide.

Isoprenoid biosynthesis pathways are generally classified into a mevalonate pathway (also referred to as MVA pathway) and a non-mevalonate pathway (also referred to as MEP pathway). The non-mevalonate pathway is a pathway of eventually generating isopentenyl diphosphate (IPP) or dimethylallyl diphosphate (DMAPP) from glyceraldehyde 3-phosphate and pyruvic acid. The host cell for use in the present invention has an isopentenyl diphosphate synthesis ability by a non-mevalonate pathway.

Another aspect of the present invention is a recombinant cell prepared by introducing a nucleic acid encoding isoprene synthase into a host cell having a function of synthesizing acetyl CoA from methyltetrahydrofolate, carbon monoxide, and CoA, wherein the nucleic acid is expressed in the host cell, and the recombinant cell is capable of producing isoprene from at least one C1 compound selected from the group consisting of carbon monoxide, carbon dioxide, formic acid, and methanol.

The recombinant cell of the present invention is prepared by introducing a nucleic acid encoding isoprene synthase into a host cell having a "function of synthesizing acetyl CoA from methyltetrahydrofolate, carbon monoxide, and CoA", and the nucleic acid is expressed in the host cell. The recombinant cell is capable of producing isoprene from at least one C1 compound selected from the group consisting of carbon monoxide, carbon dioxide, formic acid, and methanol. Also by the recombinant cell of the present invention, it is possible to synthesize IPP from the C1 compound, and further to convert the synthesized IPP to isoprene. As a result, it is possible to produce isoprene from the C1 compound. By using the recombinant cell of the present invention, it is possible to produce isoprene, for example, from syngas containing carbon monoxide and/or carbon dioxide.

Examples of the cell having a "function of synthesizing acetyl CoA from methyltetrahydrofolate, carbon monoxide, and CoA" include anaerobic microorganisms having an acetyl CoA pathway (Wood-Ljungdahl pathway) and a methanol pathway shown in FIG. 1.

Preferably, the recombinant cell has carbon monoxide dehydrogenase.

Carbon monoxide dehydrogenase (EC 1.2.99.2/1.2.7.4) (CO dehydrogenase, CODH) has an activity of generating carbon dioxide and proton from carbon monoxide and water, and an activity of generating carbon monoxide and water from carbon dioxide and proton, which is a reverse reaction. The carbon monoxide dehydrogenase is one of enzymes that act in the acetyl CoA pathway (FIG. 1).

Preferably, the host cell is a *Clostridium* bacterium or a *Moorella* bacterium.

Preferably, a nucleic acid encoding a group of enzymes acting in a mevalonate pathway is further introduced so that an isopentenyl diphosphate synthesis ability by a mevalonate pathway is further imparted.

With such a constitution, IPP that is to be a substrate for isoprene synthase is synthesized both in a mevalonate pathway and in a non-mevalonate pathway, so that IPP is supplied efficiently. As a result, the recombinant cell of the present invention has a higher isoprene producing ability.

Preferably, the mevalonate pathway is that of yeast.

Preferably, the mevalonate pathway is that of prokaryote.

Preferably, the mevalonate pathway is that of actinomycete.

Preferably, a nucleic acid encoding at least one enzyme acting in a non-mevalonate pathway is further introduced, and the nucleic acid is expressed in the host cell.

With such a constitution, an IPP synthesis ability by a non-mevalonate pathway is enhanced. As a result, the recombinant cell of the present invention has a higher isoprene producing ability.

Preferably, the non-mevalonate pathway is that of other organisms than the host cell.

Preferably, the isoprene synthase is derived from plant.

Preferably, the nucleic acid encoding isoprene synthase encodes the following (a), (b) or (c):

(a) a protein consisting of an amino acid sequence represented by SEQ ID NO: 2, (b) a protein consisting of an amino acid sequence in which 1 to 20 amino acids are deleted, substituted or added in the amino acid sequence represented by SEQ ID NO: 2, and having isoprene synthase activity, and (c) a protein consisting of an amino acid sequence having a homology of 60% or more with the amino acid sequence represented by SEQ ID NO: 2, and having isoprene synthase activity.

Preferably, the nucleic acid introduced into the host cell is codon-modified.

With such a constitution, it is possible to allow the introduced nucleic acid (foreign gene) to be expressed in the host cell more efficiently.

Preferably, the nucleic acid introduced into the host cell is incorporated in a genome of the host cell.

Preferably, the nucleic acid introduced into the host cell is incorporated in a plasmid.

Another aspect of the present invention is a method for producing isoprene by culturing the recombinant cell using at least one C1 compound selected from the group consisting of carbon monoxide, carbon dioxide, formic acid, and methanol as a carbon source, to allow the recombinant cell to produce isoprene.

The present invention relates to a method for producing isoprene. In the present invention, by culturing the recombinant cell using at least one C1 compound selected from the group consisting of carbon monoxide, carbon dioxide, formic acid, and methanol as a carbon source, the recombinant cell is allowed to produce isoprene. According to the present invention, it is possible to produce isoprene from syngas containing carbon monoxide and/or carbon dioxide, formic acid, or methanol.

Another aspect of the present invention is a method for producing isoprene by bringing at least one C1 compound selected from the group consisting of carbon monoxide, carbon dioxide, formic acid, and methanol into contact with the recombinant cell, to allow the recombinant cell to produce isoprene from the C1 compound.

In the present invention, by bringing at least one C1 compound selected from the group consisting of carbon monoxide, carbon dioxide, formic acid, and methanol into contact with the recombinant cell, the recombinant cell is allowed to produce isoprene from the C1 compound. Also according to the present invention, it is possible to produce isoprene from syngas containing carbon monoxide and/or carbon dioxide, formic acid, or methanol.

Preferably, the recombinant cell is provided with a gas mainly containing carbon monoxide and hydrogen, or a gas mainly containing carbon dioxide and hydrogen.

The wording "provide the recombinant cell with a gas" means giving to the recombinant cell a gas as a carbon source or the like, or bringing the gas into contact with the recombinant cell.

Preferably, the recombinant cell is prepared from a *Clostridium* bacterium or a *Moorella* bacterium as a host cell, and isoprene released outside the recombinant cell is recovered.

Bicarbonate may be used in place of carbon dioxide.

ADVANTAGEOUS EFFECT OF INVENTION

According to the recombinant cell of the present invention, it is possible to produce isoprene from carbon monoxide, carbon dioxide, formic acid, or methanol. For example, it is possible to produce isoprene from syngas containing carbon monoxide and/or carbon dioxide.

Similarly, according to the method for producing isoprene of the present invention, it is possible to produce isoprene from carbon monoxide, carbon dioxide, formic acid, or methanol.

DESCRIPTION OF EMBODIMENT

Figure 1:
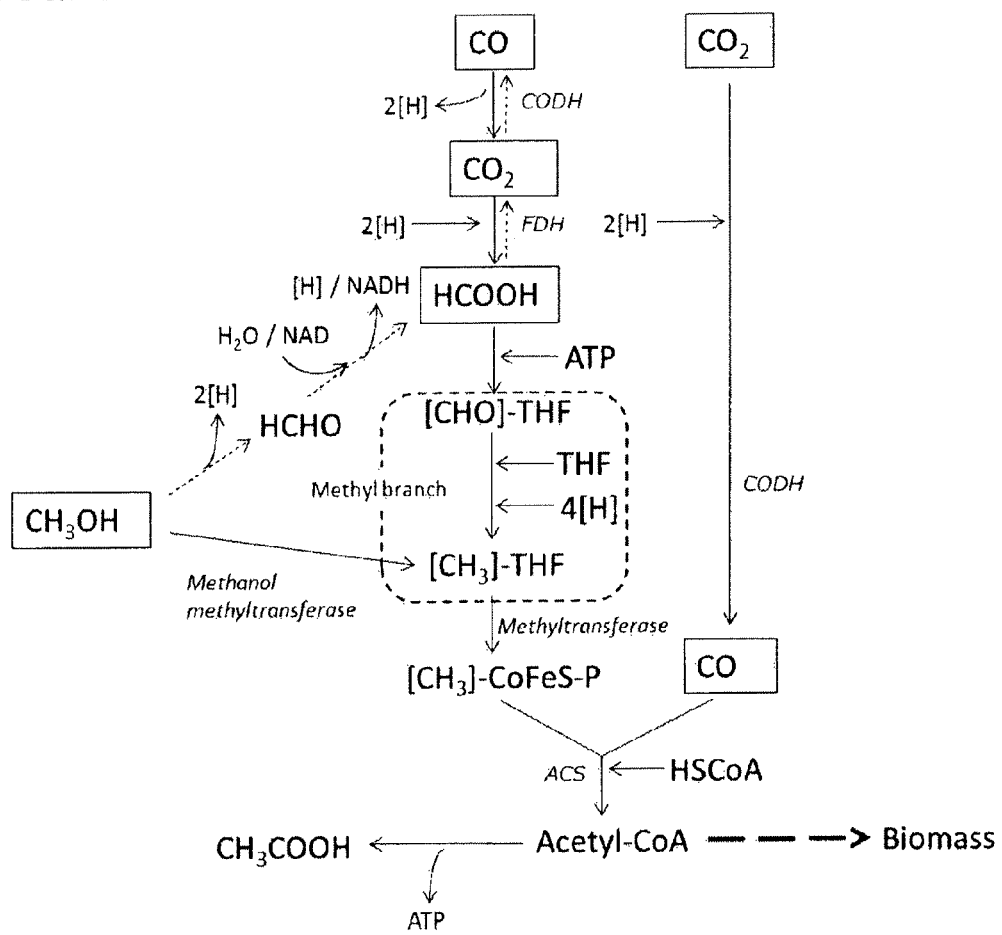
FIG. 1 is an explanatory view showing an acetyl CoA pathway and a methanol pathway.

A recombinant cell according to one aspect of the present invention is prepared by introducing a nucleic acid encoding isoprene synthase into a host cell having an isopentenyl diphosphate (IPP) synthesis ability by a non-mevalonate pathway, and the nucleic acid is expressed in the host cell, and the recombinant cell is capable of producing isoprene from at least one C1 compound selected from the group consisting of carbon monoxide, carbon dioxide, formic acid, and methanol.

The host cell in the recombinant cell of the present aspect has an "IPP synthesis ability by a non-mevalonate pathway".

As described above, synthesis pathways of IPP are generally classified into a mevalonate pathway (MVA pathway) and a non-mevalonate pathway (MEP pathway). The mevalonate pathway is inherent in eukaryotes, and starts with acetyl CoA as a starting substance. Enzymes acting in the mevalonate pathway include, in the order from the upstream, acetyl CoA acetyl transferase, HMG-CoA synthase, HMG-CoA reductase, mevalonate kinase, 5-phosphomevalonate kinase, diphosphomevalonate decarboxylase, and isopentenyl diphosphate isomerase.

On the other hand, the non-mevalonate pathway is inherent in prokaryotes and chloroplasts and plastids, and starts with glyceraldehyde 3-phosphate and pyruvic acid as starting substances. Enzymes acting in the non-mevalonate pathway include, in the order from the upstream, DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase and HMB-PP reductase.

A recombinant cell according to another aspect of the present invention is prepared by introducing a nucleic acid encoding isoprene synthase into a host cell having a function of synthesizing acetyl CoA from methyltetrahydrofolate, carbon monoxide, and CoA, and the nucleic acid is expressed in the host cell, and the recombinant cell is capable of producing isoprene from at least one C1 compound selected from the group consisting of carbon monoxide, carbon dioxide, formic acid, and methanol.

Preferably, the recombinant cell of the present invention further has carbon monoxide dehydrogenase (CODH). Specifically, a cell that grows by a function of generating carbon dioxide and proton from carbon monoxide and water mainly by carbon monoxide metabolism, namely, by the action of carbon monoxide dehydrogenase is preferred. Examples of such a cell include anaerobic microorganisms having an acetyl CoA pathway (Wood-Ljungdahl pathway) and a methanol pathway (Methanol pathway) shown in FIG. 1.

Representative examples of the anaerobic microorganisms include *Clostridium* bacteria or *Moorella* bacteria such as *Clostridium ljungdahlii*, *Clostridium autoethanogenumn*, *Clostridium carboxidivorans*, *Clostridium ragsdalei* (Kopke M. et al., Appl. Environ. Microbiol. 2011, 77(15), 5467-5475), and *Moorella thermoacetica* (same as *Clostridium thermoaceticum*) (Pierce EG. Et al., Environ. Microbial. 2008, 10, 2550-2573). In particular, *Clostridium* bacteria are preferred as the host cell in the present invention because their host-vector systems and culture methods have been established.

The five species of *Clostridium* bacteria or *Moorella* bacteria recited above are known as representative examples of syngas utilizing microorganisms.

Besides *Clostridium* bacteria and *Moorella* bacteria, *Carboxydocella sporoducens* sp. Nov. (Slepova TV. et al., Inter. J. Sys. Evol. Microbiol. 2006, 56, 797-800), *Rhodopseudomonas gelatinosa* (Uffen RL, J. Bacteriol. 1983, 155(3), 956-965), *Eubacterium limosum* (Roh H. et al., J. Bacteriol. 2011, 193(1), 307-308), *Butyribacterium methylotrophicum* (Lynd, LH. Et al., J. Bacteriol. 1983, 153(3), 1415-1423) and the like may be used as the host cell.

All of proliferation and CODH activity of the bacteria as described above are oxygen sensitive. However, oxygen insensitive CODH is also known. For example, oxygen insensitive CODH exists in other bacterial species represented by *Oligotropha carboxidovorans* (Schubel, U. et al., J. Bacteriol., 1995, 2197-2203), and *Bradyrhizobium japonicum* (Lorite MJ. Et al., Appl. Environ. Microbiol., 2000, 66 (5), 1871-1876) (King GM et al., Appl. Environ. Microbiol. 2003, 69 (12), 7257-7265). Also in *Ralsotonia* bacteria which are aerobic hydrogen oxidizing bacteria, oxygen insensitive CODH exists (NCBI Gene ID: 4249199, 8019399).

As described above, there widely exist bacteria having CODH. The host cell for use in the present invention can be appropriately selected therefrom. For example, using a selective medium containing CO, CO/$H_2$ (gas mainly containing CO and $H_2$), or CO/$CO_2$/$H_2$ (gas mainly containing CO, $CO_2$ and $H_2$) as the sole carbon source and energy source, a bacterium having CODH that is usable as the host cell can be isolated in anaerobic, microaerobic or aerobic conditions.

The isoprene synthase is not particularly limited as far as it can exert its enzyme activity in the recombinant cell. Similarly, the nucleic acid (gene) encoding isoprene synthase is not particularly limited insofar as it is normally transcribed and translated in the recombinant cell. The nucleic acid encoding isoprene synthase may be codon-modified for ease of transcription in the host cell. For example, when the host cell is a *Clostridium* bacterium, the codon of the nucleic acid to be introduced may be modified based on the information of codon usage of *Clostridium* bacteria.

Isoprene synthase is found in many plants. Specific examples of isoprene synthase include one derived from poplar (*Populus nigra*) (GenBank Accession No.: AM410988.1). Besides the above, one derived from *Bacillus subtilis* (Sivy T L. et al., Biochem. Biophys. Res. Commu. 2002, 294(1), 71-5) can be recited.

SEQ ID NO: 1 shows a nucleotide sequence of a nucleic acid (DNA) encoding the isoprene synthase derived from poplar and a corresponding amino acid sequence. SEQ ID NO: 2 shows only the amino acid sequence. DNA having the nucleotide sequence represented by SEQ ID NO: 1 is one example of the nucleic acid encoding isoprene synthase.

Further, the nucleic acid encoding isoprene synthase includes at least a nucleic acid encoding the following (a), (b) or (c):

(a) a protein consisting of an amino acid sequence represented by SEQ ID NO: 2, (b) a protein consisting of an amino acid sequence in which 1 to 20 amino acids are deleted, substituted or added in the amino acid sequence represented by SEQ ID NO: 2, and having isoprene synthase activity, and (c) a protein consisting of an amino acid sequence having a homology of 60% or more with the amino acid sequence represented by SEQ ID NO: 2, and having isoprene synthase activity.

The homology of an amino acid sequence in (c) is more preferably 80% or more, further preferably 90% or more, and particularly preferably 95% or more.

In the recombinant cell of the present invention, other nucleic acid may be further introduced in addition to the nucleic acid encoding isoprene synthase. In one embodiment, a nucleic acid encoding a group of enzymes acting in a mevalonate pathway is further introduced, so that an IPP synthesis ability by a mevalonate pathway is further imparted. According to this constitution, since IPP is synthesized both in a mevalonate pathway and in a non-mevalonate pathway, the IPP synthesis ability is enhanced, and as a result, isoprene is produced more efficiently.

As described above, as the group of enzymes acting in a mevalonate pathway, acetyl CoA acetyl transferase, HMG-CoA synthase, HMG-CoA reductase, mevalonate kinase, 5-phosphomevalonate kinase, diphosphomevalonate decarboxylase, and isopentenyl diphosphate isomerase be recited. A nucleic acid to be introduced may be selected among these so that a group of enzymes consisting, for example, of HMG-CoA synthase, HMG-CoA reductase, mevalonate kinase, 5-phosphomevalonate kinase, diphosphomevalonate decarboxylase, and isopentenyl diphosphate isomerase is expressed in the host cell. Also with regard to such a nucleic acid, one that is codon-modified for ease of transcription in the host cell may be employed.

The mevalonate pathway is inherent in all eukaryotes, but is also found in prokaryotes. As prokaryotes having a mevalonate pathway, *Streptomyces* sp. Strain CL190 (Takagi M. et al., J. Bacteriol. 2000, 182 (15), 4153-7), and *Streptomyces griseolosporeus* MF730-N6 (Hamano Y. et al., Biosci. Biotechnol. Biochem. 2001, 65(7), 1627-35) are recited with respect to actinomycetes.

With respect to bacteria, *Lactobacillus helveticus* (Smeds A et al., DNA seq. 2001, 12(3), 187-190), *Corynebacterium amycolatum, Mycobacterium marinum, Bacillus coagulans, Enterococcus faecalis, Streptococuss agalactiae, Myxococcus xanthus* and so on are recited (Lombard J. et al., Mol. Biol. Evol. 2010, 28(1), 87-99).

With respect to archaea, genus *Aeropyrum*, genus *Sulfolobus*, genus *Desulfurococcus*, genus *Thermoproteus*, genus *Halobacterium*, genus *Methanococcus*, genus *Thermococcus*, genus *Pyrococcus*, genus *Methanopyrus*, genus *Thermoplasma* and so on are recited (Lombard J. et al., Mol. Biol. Evol. 2010, 28(1), 87-99).

The origin of the group of enzymes acting in a mevalonate pathway is not particularly limited, however, a group of enzymes acting in a mevalonate pathway of yeast is preferred. Also, a group of enzymes acting in a mevalonate pathway of actinomycete is preferably employed.

In another embodiment, a nucleic acid encoding at least one enzyme acting in a non-mevalonate pathway is further introduced, and the nucleic acid is expressed in the host cell. Also in this embodiment, the IPP synthesis ability is enhanced, and as a result, isoprene is produced more efficiently. One nucleic acid or two or more nucleic acids may be introduced.

As described above, the enzymes acting in a non-mevalonate pathway include DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase, and HMB-PP reductase. For example, one enzyme or two or more enzymes may be selected from the above group of enzymes, and then a nucleic acid encoding the selected enzymes may be introduced into the host cell.

The enzymes acting in a non-mevalonate pathway are preferably derived from other organisms than the host cell. With such a constitution, it is possible to avoid reaction suppression by a reaction product.

Also with regard to such a nucleic acid, one that is codon-modified for ease of transcription in the host cell may be employed.

The enzymes acting in a mevalonate pathway or in a non-mevalonate pathway may be naturally occurring enzymes or enzymes modified therefrom. For example, amino acid substitution variants of each enzyme, and polypeptides that are partial fragments of each enzyme and have equivalent enzyme activity are also applicable.

The technique for introducing a nucleic acid into the host cell is not particularly limited, and can be appropriately selected depending on the kind of the host cell and the like. For example, a vector that can be introduced into the host cell and can allow expression of the nucleic acid incorporated therein may be used.

For example, when the host cell is a prokaryote such as a bacterium, a vector that can self duplicate or can be incorporated in chromosome in the host cell, and contains a promoter at the position allowing transcription of the inserted nucleic acid (DNA) may be used. For example, it is preferred to construct in the host cell a series of structures including a promoter, a ribosome binding sequence, the above nucleic acid (DNA) and a transcription termination sequence by using the vector.

In the case where the host cell is a *Clostridium* bacterium (including related species such as *Moorella* bacteria), a shuttle vector pIMP1 between *Clostridium* bacterium and *Escherichia coli* (Mermelstein LD et al., Bio/technology 1992, 10, 190-195) may be used. The shuttle vector is a fusion vector of pUC9 (ATCC 37252) and pIM13 isolated from *Bacillus subtilis* (Projan SJ et al., J. Bacteriol. 1987, 169 (11), 5131-5139) and is retained stably in the *Clostridium* bacterium.

For gene introduction into the *Clostridium* bacterium, an electroporation method is generally used. However, the introduced exogenous plasmid immediately after gene introduction is liable to be decomposed by a restriction enzyme Cac824I and the like, and is therefore very instable. For this reason, it is preferred to once amplify the vector from pIMP1 in *Escherichia coli*, for example, strain ER2275 having pAN1 (Mermelstein LD et al., Apply. Environ. Microbiol. 1993, 59(4), 1077-1081) carrying a methyl transferase gene from *Bacillus subtilis* phage Φ3T1, followed by a methylation treatment, and to recover the resultant vector from *Escherichia coli* for use in transformation by electroporation. Recently, Cac824I gene-deficient *Clostridium acetobuthylicum* has been developed, and make it possible to stably carry a vector which is not subjected to a methylation treatment (Dong H. et al., PLoS ONE 2010, 5 (2), e9038).

Examples of the promoter for heterologous gene expression in *Clostridium* bacteria include thl (thiolase) promoter (Perret S et al., J. Bacteriol. 2004, 186(1), 253-257), Dha (glycerol dehydratase) promoter (Raynaud C. et al., PNAS 2003, 100(9), 5010-5015), ptb (phosphotransbutyrylase) promoter (Desai R P et al., Appl. Environ. Microbial. 1999, 65(3), 936-945), and adc (acetoacetate decarboxylase) promoter (Lee J et al., Appl. Environ. Microbial. 2012, 78 (5), 1416-1423). However, in the present invention, sequences of promoter regions used in operons of various metabolic systems found in the host cell or the like may be used without limited to the above examples.

For introducing plural kinds of nucleic acids into the host cell by using a vector, the nucleic acids may be incorporated in one vector, or incorporated in individual vectors. When plural kinds of nucleic acids are incorporated in one vector, these nucleic acids may be expressed under a common promoter for these nucleic acids, or expressed under individual promoters. As an exemplary form of introducing plural kinds of nucleic acids, a mode of introducing "a nucleic acid encoding a group of enzymes acting in a mevalonate pathway" and "a nucleic acid encoding at least one enzyme acting in a non-mevalonate pathway" in addition to "a nucleic acid encoding isoprene synthase" can be recited.

By further conducting mutation or genome shuffling in addition to the introduction of exogenous nucleic acid as described above, it is possible to breed a bacterial strain exhibiting dramatically increased productivity of isoprene.

That is, in the present invention, an exogenous nucleic acid may be incorporated in a genome of the host cell or incorporated in a plasmid.

In one aspect of the method for producing isoprene of the present invention, the recombinant cell is cultured using at least one C1 compound selected from the group consisting of carbon monoxide, carbon dioxide, formic acid, and methanol as a carbon source, to allow the recombinant cell to produce isoprene. The C1 compound used as a carbon source may be used singly or in combination of two or more. The C1 compound is preferably used as a main carbon source, and more preferably as the sole carbon source.

Also, it is preferred to provide hydrogen ($H_2$) concurrently as an energy source.

The method for culturing the recombinant cell of the present invention is not particularly limited, and may be appropriately conducted depending on the kind of the host cell and the like. When the recombinant cell is a Clostridium bacterium (strictly anaerobic), it is cultured, for example, in a nutrient condition including inorganic salts required for growth, and syngas. Preferably, it is cultured under a pressurized condition at about 0.2 to 0.3 MPa (absolute pressure). Further, for improving initial proliferation and attained cell density, small amounts of organic substances such as vitamin, yeast extract, corn steep liquor, and Bacto Tryptone may be added.

When the recombinant cell is aerobic or obligately anaerobic, for example, it may be cultured in a liquid medium under aeration and stirring.

In another aspect of the method for producing isoprene of the present invention, at least one C1 compound selected from the group consisting of carbon monoxide, carbon dioxide, formic acid, and methanol is brought into contact with the recombinant cell, to allow the recombinant cell to produce isoprene from the C1 compound. That is, regardless of whether or not cell division (cell proliferation) associates, it is possible to bring the C1 compound into contact with the recombinant cell, to produce isoprene. For example, the C1 compound may be continuously supplied to an immobilized recombinant cell to continuously produce isoprene.

Also in the present aspect, the C1 compound may be used singly or in combination of two or more. It is preferred to bring hydrogen ($H_2$) into contact concurrently as an energy source.

In a preferred embodiment, the recombinant cell is provided with a gas mainly containing carbon monoxide and hydrogen, or a gas mainly containing carbon dioxide and hydrogen. In other words, isoprene is produced from carbon monoxide or carbon dioxide in such a gas by culturing the recombinant cell by using the gas as a carbon source, or by bringing the gas into contact with the recombinant cell. Also in this case, hydrogen is used as an energy source.

Isoprene may be produced from formic acid and/or methanol by providing the recombinant cell with formic acid and/or methanol. In other words, isoprene can also be produced from formic acid and/or methanol by culturing the recombinant cell using, as a carbon source, formic acid or methanol solely or in addition to carbon monoxide and/or carbon dioxide, or by bringing formic acid and/or methanol into contact with the recombinant cell.

The produced isoprene is accumulated in the cell or released outside the cell. For example, by using the recombinant cell prepared from a host cell of a Clostridium bacterium or a Moorella bacterium, and recovering isoprene released outside the cell, followed by isolation and purification, purified isoprene can be obtained.

Bicarbonate can be sometimes used in place of carbon dioxide. In other words, Clostridium bacteria and related species are known to have carbonic anhydrase (CA) (EC 4.2.1.1: $H_2O+CO_2 \Leftrightarrow HCO_3^-+H^+$) (Braus-Stromeyer SA et al., J. Bacteriol. 1997, 179(22), 7197-7200). Bicarbonate such as $NaHCO_3$ which is a source of $HCO_3^-$ can be used as a $CO_2$ source.

Herein, combinations of carbon monoxide, carbon dioxide, formic acid, and methanol that can be provided to the recombinant cell in the case where the host cell has the acetyl CoA pathway and the methanol pathway (FIG. 1) are described.

In acetyl CoA synthesis by the acetyl CoA pathway, a synthesis process of acetyl CoA from CoA, methyltetrahydrofolate ($[CH_3]$-THF), and CO by the actions of methyltransferase, Corrinoid iron-sulfur protein (CoFeS-P), acetyl CoA synthase (ACS), and CODH is essential (Ragsdale SW et al., B.B.R.C. 2008, 1784(12), 1873-1898).

On the other hand, it is known that adding formic acid and/or methanol besides CO and/or $CO_2$ as a carbon source in culturing of Butyribacterium methylotrophicum increases the content of tetrahydrofolate in CO metabolism, namely, methyl branch in the acetyl CoA pathway, and activities of CODH, formate dehydrogenase (FDH) and hydrogenase required in CO metabolism (Kerby R. et al., J. Bacteriol. 1987, 169(12), 5605-5609). Also in Eubacterium limosum or the like, it is demonstrated that high proliferation is achieved by using $CO_2$ and methanol as a carbon source in an anaerobic condition (Genthner BRS. et al., Appl. Environ. Microbial., 1987, 53(3), 471-476).

The influence of methanol on syngas utilizing microorganisms, and the results of genome analysis of Moorella thermoacetica (Clostridium thermoaceticum), Clostridium ljungdahlii and the like (Pierce E. et al., Environ. Microbiol. 2008, 10(10), 2550-2573; Durre P. et al., PNAS 2010, 107(29), 13087-13092) can give an explanation for involvement of the methanol pathway as shown in FIG. 1 as, a donor of a methyl group in the acetyl CoA pathway (Wood-Ljungdahl pathway) in these microorganism species.

Actually in some Clostridium bacteria, the forward activity of formate dehydrogenase (FDH) (EC 1.2.1.2/1.2.1.43: Formate+NAD(P)$^+$ $\Leftrightarrow$ $CO_2$+NAD(P)H) (formation of $CO_2$ from formate) is confirmed (Liu C L et al., J. Bacteriol. 1984, 159(1), 375-380; Keamy J J et al., J. Bacteriol. 1972, 109(1), 152-161). Therefore, in these strains, a reaction in the direction of generating $CO_2$ from methanol ($CH_3OH$) and/or formic acid (HCOOH) can partly proceed when $CO_2$ and/or CO is deficient (FIG. 1). This can also be explained by the phenomenon that formate dehydrogenase activity and CODH activity increase by addition of $CH_3OH$ (Kerby R et al., J. Bateriol. 1987, 169(12), 5605-5609) as described above. In other words, these can be proliferated with formic acid (HCOOH) or methanol ($CH_3OH$) as the sole carbon source.

Even if the host cell strain inherently lacks the forward activity of formate dehydrogenase, it may be provided with the forward activity by gene modification such as introduction of mutation, introduction of foreign gene, or genome shuffling.

For these reasons, it is possible to produce isoprene using the following gas or liquid when the host cell has the acetyl CoA pathway and the methanol pathway.

CO
$CO_2$
$CO/H_2$
$CO_2/H_2$
$CO/CO_2/H_2$
CO/HCOOH
$CO_2$/HCOOH
$CO/CH_3OH$
$CO_2/CH_3OH$
$CO/H_2$/HCOOH
$CO_2/H_2$/HCOOH
$CO/H_2/CH_3OH$
$CO_2/H_2/CH_3OH$
$CO/CO_2/H_2$/HCOOH
$CO/CO_2/H_2/CH_3OH$
$CH_3OH/H_2$
HCOOH/$H_2$
$CH_3OH$
HCOOH

When the recombinant cell of the present invention is cultured exclusively for cell proliferation, rather than for production of isoprene, it is not necessary to use carbon monoxide and/or carbon dioxide as a carbon source. For example, the recombinant cell may be cultured using other carbon sources such as saccharides or glycerin.

In the following, the present invention will be described more specifically by way of examples. However, the present invention is not limited to these examples.

EXAMPLE 1

(1) Isolation of Isoprene Synthase Gene from Poplar, and Construction of Expression Vector Using total RNA derived from leaf of poplar (*Populus nigra*) as a template, a nucleic acid encoding isoprene synthase (IspS) from poplar (IspS gene from poplar, SEQ ID NO: 1, GenBank Accession No.: AM410988.1) was amplified by RT-PCR using primers represented by SEQ ID NO: 3 and SEQ ID NO: 4. The obtained amplified DNA fragment was cloned into pT7-Blue T vector (TAKARA BIO INC.) to construct pT7IS.

On the other hand, in BamHI/EcoRI site of *Clostridium/E. coli* shuttle vector pIMP1 (Mermelstein LD et al., Bio/technology 1992, 10, 190-195), synthetic DNAs represented by SEQ ID NO: 5 and SEQ ID NO: 6 were introduced to modify the cloning site, to construct pIM1A. Further, in PstI/BamHI site of pIM1A, synthetic DNAs represented by SEQ ID NO: 7 and SEQ ID NO: 8 were introduced to construct pIM1B. The pT7IS was cut with BamHI to obtain IspS gene. The IspS gene was introduced into BamHI site of pIM1B to construct a vector pIMBIS to express poplar IspS.

In this expression vector, a promoter and a terminator region derived from pSOS95 (Mingardon F et al., Appi. Environ. Microbiol. 2005, 71(3), 1215-1222) lie upstream and downstream of the IspS gene, respectively.

(2) Preparation of Recombinant Having Isoprene Producing Ability

By transforming *E. coli* ER2275 (NEB), into which pAN1 encoding methyl transferase gene from *Bacillus subtilis* phage φ3TI (Mermelstein LD et al., Appl. Environ. Microbiol., 1993, 59(4), 1077-1081) was introduced, with pIMBIS prepared in the above (1), in vivo methylation was conducted. Methylated pIMBIS was recovered from transformed *E. coli* ER2275. According to the method described in "BIO/TECHNOLOGY 1992, VOL. 10, 190-195", *Clostridium ljungdahlii* (DSM13528/ATCC55383) was transformed with the methylated pIMBIS by electroporation to obtain a recombinant.

(3) Isoprene Production by Recombinant

The recombinant of *C. ljungdahlii* obtained in the above (2) was cultured at 37° C. in an aerobic condition. As a culture medium, ATCC medium 1754 PETC medium containing 5 μg/mL of Clarithromycin and 20 μg/mL of Thiamphenicol (but not containing fructose and yeast extract) was used. A 100 mL-volume hermetically-sealable glass vessel was charged with 10 mL of culture medium, and filled with an oxygen-free gas at a gas pressure of 2.5 atmospheric pressure (absolute pressure), and hermetically sealed with an aluminum cap, and then shaking culture was conducted. As the oxygen-free gas, one of three mixed gases of (a) $CO/H_2$=50/50%, (b) $CO/CO_2/H_2$=33/33/34%, and (c) $CO_2/H_2$=50/50% (volume ratio in each case) was used.

As a control, a recombinant into which pIMB1 was introduced in place of pIMBIS was cultured in the same manner.

The gas phase component after end of the culture was analyzed by GC/MS.

As a result, in the recombinant into which pIMBIS was introduced, isoprene was detected in every case using any mixed gas. On the other hand, in the recombinant of the control, isoprene was not detected in any case.

These revealed that isoprene was produced from syngas by culturing the recombinant of *Clostridium ljungdahlii* into which isoprene synthase gene from poplar was introduced.

EXAMPLE 2

(1) Construction of Expression Vector into which Mevalonate Pathway Enzyme Gene and Isoprene Synthase Gene were Introduced Using genome DNA of *Streptomyces griseolosporeus* (*Kitasatospora griseola*) as a template, a nucleic acid encoding mevalonate pathway enzymes of *S. griseolosporeus* (SEQ ID NO: 9) was amplified by PCR using primers represented by SEQ ID NO: 10 and SEQ ID NO: 11. This nucleic acid includes a gene cluster encoding mevalonate kinase, mevalonate diphosphate decarboxylase, phosphomevalonate kinase, IPP isomerase, HMG-CoA (3-hydroxy-3-methylglutaryl coenzyme A) reductase (HMGR), and HMG-CoA synthase. The obtained amplified DNA fragment was cloned into pT7-Blue T vector to construct pT7SMV.

On the other hand, using pT7IS prepared in Example 1 as a template, a DNA fragment containing IspS gene from poplar was amplified by using primers represented by SEQ ID NO: 3 and SEQ ID NO: 12. This DNA fragment was cloned into pT7-Blue T vector to construct pT7IS2.

In BamHI/EcoRI site of pIM1B prepared in Example 1, double-stranded DNA composed of oligo DNAs of SEQ ID NO: 13 and SEQ ID NO: 14 was introduced to construct pIM1C. On the other hand, pT7IS2 was cut with BamHI and KpnI to obtain a DNA fragment containing IspS gene. This DNA fragment was introduced into BamHI/KpnI site of pIM1C to construct pIMCIS.

Further, pT7SMV was cut with KpnI to obtain an insert DNA fragment. This DNA fragment was introduced in KpnI site of pIMCIS to construct pIMCISMV. pIMCISMV has genes encoding isoprene synthase derived from poplar, and the group of mevalonate pathway enzymes derived from *Streptomyces*. Expression of these genes in pIMCISMV is regulated by a promoter and a terminator derived from pSOS95 (Mingardon F et al., Appl. Envirion. Microbiol. 2005, 71 (3), 1215-1222).

(2) Preparation of Recombinant Having Isoprene Producing Ability

*Clostridium ljungdahlii* (DSM13528/ATCC55383) was transformed with pIMCISMV subjected to a methylation treatment, in the same manner as in Example 1, to obtain a recombinant.

(3) Isoprene Production by Recombinant

The recombinant transformed with pIMCISMV was cultured by using any one of three kinds of mixed gases in the same manner as in Example 1.

As a control, a recombinant into which pIM1C was introduced in place of pIMCISMV, and a recombinant having pIMBIS prepared in Example 1 were cultured in the same manner.

The gas phase component after end of the culture was analyzed by GC/MS.

As a result, in the recombinant into which pIMCISMV was introduced (present example) and in the recombinant into which pIMBIS was introduced (Example 1), isoprene was detected in any case using any mixed gas. Regarding the isoprene production, the recombinant into which pIMCISMV was introduced (present example) produced isoprene twice to four times the amount of isoprene produced by the recombinant into which pIMBIS was introduced (Example 1). In the recombinant into which pIM1C was introduced, isoprene was not detected.

These revealed that the production amount of isoprene by the recombinant was enhanced by introducing the mevalonate pathway enzyme gene in addition to the isoprene synthase gene.

EXAMPLE 3

(1) Construction of Expression Vector into which Codon-Modified Isopentenyl Diphosphate Isomerase (IDI) Gene and Isoprene Synthase (IspS) Gene were Introduced In the present example, production of isoprene by *Clostridium ljungdahlii* into which both codon-modified isopentenyl diphosphate isomerase (IDI) gene from *Escherichia coli* and isoprene synthase (IspS) gene from poplar were introduced was attempted. For codon modification, Codon Usage Table of *Clostridium kluyveri* (DSM 555) was referred (http://www.kazusa.or.jp/codon/cgi-bin/spsearch.cgi?species=clostridium&c=i).

In PstI/BamHI site of pIM1A prepared in Example 1, codon-modified IDI-IspS operon synthetic gene (SEQ ID NO: 15, shown by sense strand) was introduced to construct an expression vector pIMAIS1. In the same manner, codon-unmodified IDI-IspS operon synthetic gene was introduced to construct an expression vector pIMAIS2.

In SEQ ID NO: 15, the part spanning nucleotide numbers 165 to 713 corresponds to codon-modified IDI gene from *Escherichia coli*, and the part spanning nucleotide numbers 780 to 2567 corresponds to codon-modified IspS gene from poplar.

The nucleotide sequence of IDI gene from *Escherichia coli* before codon modification is shown in SEQ ID NO: 16. The nucleotide sequence of IspS gene from poplar before codon modification is as shown in SEQ ID NO: 1.

(2) Preparation of Recombinant Having Isoprene Producing Ability

*Clostridium ljungdahlii* (DSM13528) was transformed with pIMAIS1 and pIMAIS2 subjected to a methylation treatment, in the same manner as in Example 1, to obtain recombinants IS1 and IS2, respectively.

(3) Isoprene Production by Recombinants

The recombinants IS1 and IS2 were cultured by using three kinds of mixed gases in the same manner as in Example 1. The gas phase component after end of the culture was analyzed by GC/MS.

As a result, isoprene production by IS1 was 1.8 to 3.0 times that by IS2 in any gas composition. These revealed that the isoprene productivity in *C. ljungdahlii* was improved by modifying codons of both enzyme genes of IDI from *Escherichia coli* and IspS from poplar.

EXAMPLE 4

Preparation of Recombinant *C. ljungdahlii* Expressing Isoprene Synthase (IspS) from *Populus alba* and Isopentenyl Diphosphate Isomerase (IDI) from Yeast, and Generation of Isoprene by the Same Gene sequences of IspS from *Populus alba* (GenBank accession no. Q50L36) and IDI from yeast were codon optimized using the codon usage pattern of *C. acetobutylicum* (SEQ ID NO: 17). For expression of heterologous gene in Clostridia, the codon optimized IspS (SEQ ID NO: 17) and IDI gene were cloned into an *Escherichia coli/Clostridium* shuttle vector pSCi01 (SEQ ID NO: 18). The IspS gene and IDI gene were inserted between the inducible tetracycline promoter and fdx transcription terminator (Nariya H. et al., Appl. Environ. Microbiol., 2011 (77), 1375). As a result, an expression vector pSCi::idi-isps (SEQ ID NO: 19) in which expression of IspS and IDI was induced by anhydrotetracycline was constructed. Plasmid was amplified in *Escherichia coli* strain NEB Express (NEB). By being amplified in this host (DCM−, DAM+), the plasmid exhibits the right methylation pattern, and can transform *C. ljungdahlii* efficiently.

*C. ljungdahlii* (DSMZ No. 13528) was cultured under strict anaerobic conditions in YTF medium (16 g tryptone, 10 g yeast extract, 4 g NaCl, 2 mM cysteine and 5 g fructose/L, pH 5.9-6). For introduction of the pSCi::idi-ispS vector into *C. ljungdahlii* by electroporation, the cells were grown in YTF medium supplemented with 40 mM D, L-threonine to OD600 of 0.2-0.3 and then washed with a SMP buffer (270 mM sucrose, 1 mM $MgCl_2$, 7 mM sodium phosphate, pH 6) and resuspended in 0.5 mL of SMP buffer containing 10% DMSO. For electroporation, 3 μg of pSCi::idi-ispS plasmid DNA was employed. A BioRad Micropulser™ electroporator system (Bio-Rad Laboratories) was used with the following setting: cuvette size 0.1 mm, voltage 0.625 kV, resistance 600Ω and capacity 25 μF. After 12 hours of regeneration in 1 mL of YTF medium, the cells were transferred to 25 mL of YTF medium containing 4 μg/mL clarithromycin and 4 μg/mL thiamphenicol. In a next step, 5-10 mL of the cell suspension was mixed with 20 mL of molten YTF-agar (1.5% agar) and cultured for 3-5 days until colonies appeared. Individual clones were picked from agar plates and liquid cultured in YTF medium (supplemented with 4 µg/mL clarithromycin and 4 µg/mL thiamphenicol).

For syngas fermentation, the cultures were transferred to ATCC 1754 medium (supplemented with 4 µg/mL clarithromycin and 4 µg/mL thiamphenicol) containing syngas (60% CO, 10% $CO_2$, 30% $H_2$) as the sole carbon source and energy source, and cultured in 50 mL of culture liquid in hermetically-sealed 200 mL glass bottle under a syngas pressure of 2 atmospheric pressure (absolute pressure). For isoprene generation analysis a GC/MS/MS-system TQ8030 (Shimadzu) equipped with a SPME (solid-phase-microextraction) analysis system available from Gerstel was used. For sampling out of a 200 mL bottle culture, 75 µm CAR/PDMS fiber (Sulpelco-Sigma Aldrich) was employed. Sampling was performed for 30 minutes at 22° C. After fiber injection into KAS6 (Gerstel), thermal desorption at 200° C. was performed for 30 seconds. A ZB-624 column available from Phenomenex (30 m length; inner diameter 0.25 mm I.D.; 1.4 µm film thickness) was used to separate the gas components. The GC/MS/MS analysis parameters were set as follows.

TABLE 1

| | Gas chromatograph | Mass Spectrum |
| --- | --- | --- |
| Starting temperature | 40° C. | 200° C./250° C. (ion source/Interface) |
| 1. Step | 40° C., 1.0 min | Ion detection starts after 1 min |
| 2. Step | Ramp with 40° C./min to 200° C. | MRM (multiple reaction monitoring); isoprene 68.1 > 67.0 (CE 13) and 67.1 > 41.0 (CE 10) - (parent ion > daughter ion); event time 0.3 sec |
| 3. Step | 200° C., 5 min | |

After thermal desorption, the fiber was treated at 300° C. for 30 minutes by the next use. The mass spectrometer was operated in MRM (multiple reaction monitoring) mode. Two transitions were selected for isoprene: 68.1 m/z to 67.0 m/z and 67.1 m/z to 41.0 m/z, and argon was used as CID (collision induced dissociation) gas. As an isoprene standard, isoprene (Sigma Aldrich cat no. I19551 (99% purity)) was used.

Figure 2:
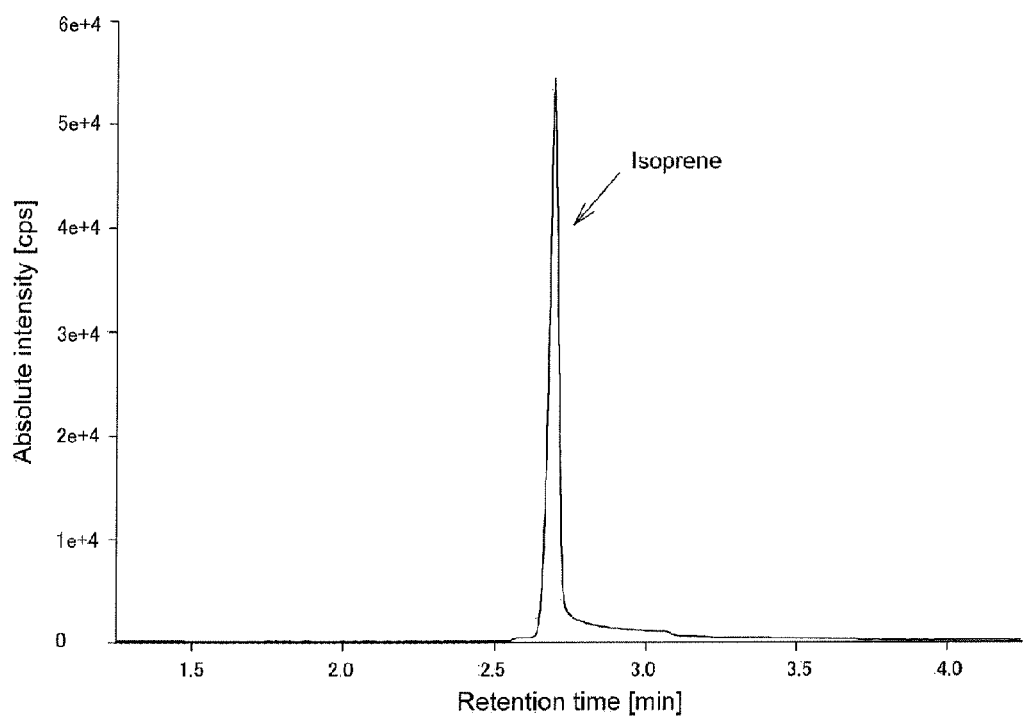
FIG. 2 is a gas chromatogram of an isoprene standard.
Figure 3:
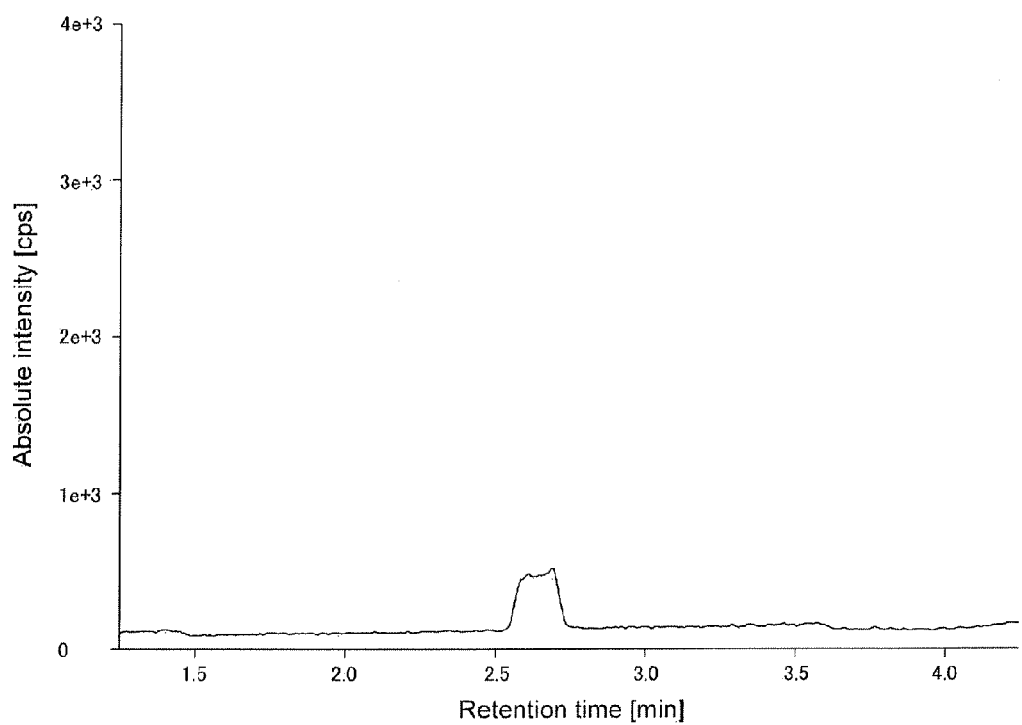
FIG. 3 is a gas chromatogram of a syngas fermentation gas phase component of *C. ljungdahlii* carrying control vector pSCi01 plasmid.
Figure 4:
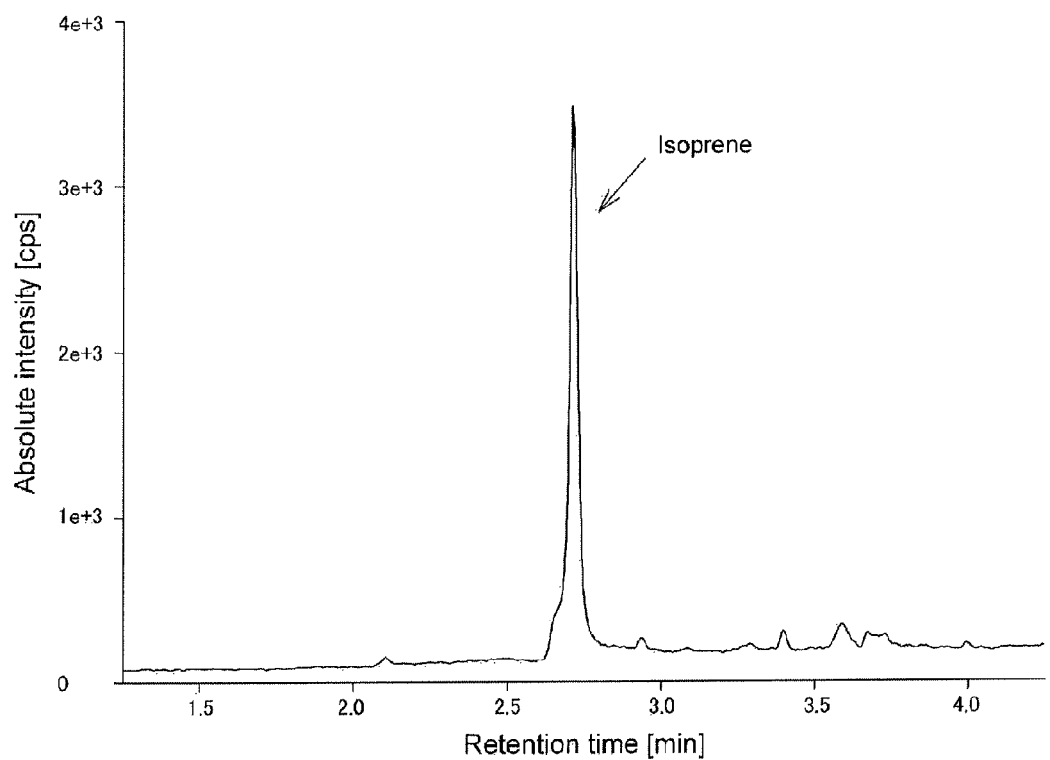
FIG. 4 is a gas chromatogram of a syngas fermentation gas phase component of *C. ljungdahlii* carrying pSCi::idi-ispS plasmid.

As shown in FIG. 2, the isoprene standard showed a retention time of 2.7 minutes and a characteristic mass transition pattern of 68.1 m/z to 67.0 m/z and 67.1 m/z to 41.0 m/z. After 48 hours from start of syngas fermentation, a head space sample was taken and analyzed by GC/MS/MS. FIG. 3 shows a result of GC/MS/MS analysis in *C. ljungdahlii* carrying pSCi01 plasmid. FIG. 4 shows a result of GC/MS/MS analysis in *C. ljungdahlii* carrying pSCi::idi-ispS plasmid.

These results demonstrated that *C. ljungdahlii* carrying pSCi::idi-ispS generated isoprene.

EXAMPLE 5

Figure 5:
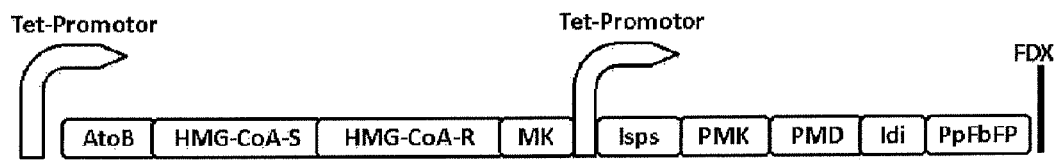
FIG. 5 is an explanatory view showing a structure of an isoprene synthesis gene cluster of plasmid pSCi::MVA-IspS-idi.

Preparation of Recombinant *C. ljungdahlii* into which IspS from *Populus alba*, IDI from *Escherichia coli*, and Microbial MVA (Mevalonate) Pathway Genes were Introduced, and Generation of Isoprene by the Same FIG. 5 and SEQ ID NO: 20 show the design of the isoprene synthesis gene cluster of plasmid pSCi::MVA-IspS-idi. Accession numbers, abbreviations and source organisms of the codon optimized genes are listed in the following table.

TABLE 2

| Gene (accession number) | Abbreviation | source |
| --- | --- | --- |
| Thiolase (NP_416728) | AtoB | *Escherichia coli* |
| HMG-CoA-Synthase (YP_041971) | HMG-CoA-S | *Staphylococcus aureus* |
| HMG-CoA-Reductase (YP_001561318) | HMG-CoA-R | *Delftia acidovorans* |
| Mevalonate kinase (NP_633786) | MK | *Methanosarcina mazei* |
| Phosphomevalonate kinase (WP_010821499) | PMK | *Enterococcus faecalis* |
| Phosphomevalonate decarboxylase (WP_010730712) | PMD | *Enterococcus faecalis* |
| Isopentenyl diphosphate isomerase (YP_003000452) | idi | *Escherichia coli* |
| Isoprene synthase (Q50L36) | IspS | *Populus alba* |
| FMN-based fluorescent proteins (AEV23113) | PpFbFP | *Pseudomonas putida* |

The MVA-IspS-idi gene cluster was inserted between the inducible tetracycline promoter and the fdx transcription terminator resulting in an anhydrotetracycline inducible expression system. Correct transgene expression from the constructed expression vector was assessed by targeted proteomics. Plasmid was amplified in *Escherichia coli* strain NEB Express (NEB)

*C. ljungdahlii* (DSMZ No. 13528) was cultured under strict anaerobic conditions in YTF medium (16 g tryptone, 10 g yeast extract, 4 g NaCl, 2 mM cysteine and 5 g fructose/L, pH 5.9-6). For introduction of the pSCi::MVA-IspS-idi vector into *C. ljungdahlii* by electroporation, the cells were grown in YTF medium supplemented with 40 mM D,L-threonine to OD600 of 0.2-0.3 and washed with a SMP buffer (270 mM sucrose, 1 mM $MgCl_2$, 7 mM sodium phosphate, pH 6) and resuspended in 0.5 mL of SMP buffer containing 10% DMSO. For electroporation 3 µg of pSCi::MVA-IspS-idi plasmid DNA was employed. A BioRad Micropulser™ electroporator system (Bio-Rad Laboratories) was used with the following setting: cuvette size 0.1 mm, voltage 0.625 kV, resistance 600Ω, and capacity 25 µF. After 12 hours of regeneration in 1 mL of YTF medium the cells were transferred to 25 mL of YTF medium containing 4 µg/mL clarithromycin and 4 µg/mL thiamphenicol. In a next step 5-10 mL of the cell suspension was mixed with 20 mL of molten YTF-agar (1.5% agar) and cultured for 3-5 days until colonies appeared. Individual clones were picked from agar plates and liquid cultured in YTF medium (supplemented with 4 µg/mL clarithromycin and 4 µg/mL thiamphenicol).

For syngas fermentation, the cultures were transferred to ATCC 1754 medium (supplemented with 4 µg/mL clarithromycin and 4 µg/mL thiamphenicol) containing syngas (60% CO, 10% $CO_2$, 30% $H_2$) as the sole carbon source and energy source, and cultured in 50 mL of culture liquid in hermetically-sealed 200 mL glass bottle under a syngas pressure of 2 atmospheric pressure (absolute pressure). After 48 hours from start of syngas fermentation, a head space sample was taken in the same manner as in Example 4, and analyzed by GC/MS/MS in the same condition as in Example 4.

Figure 6:
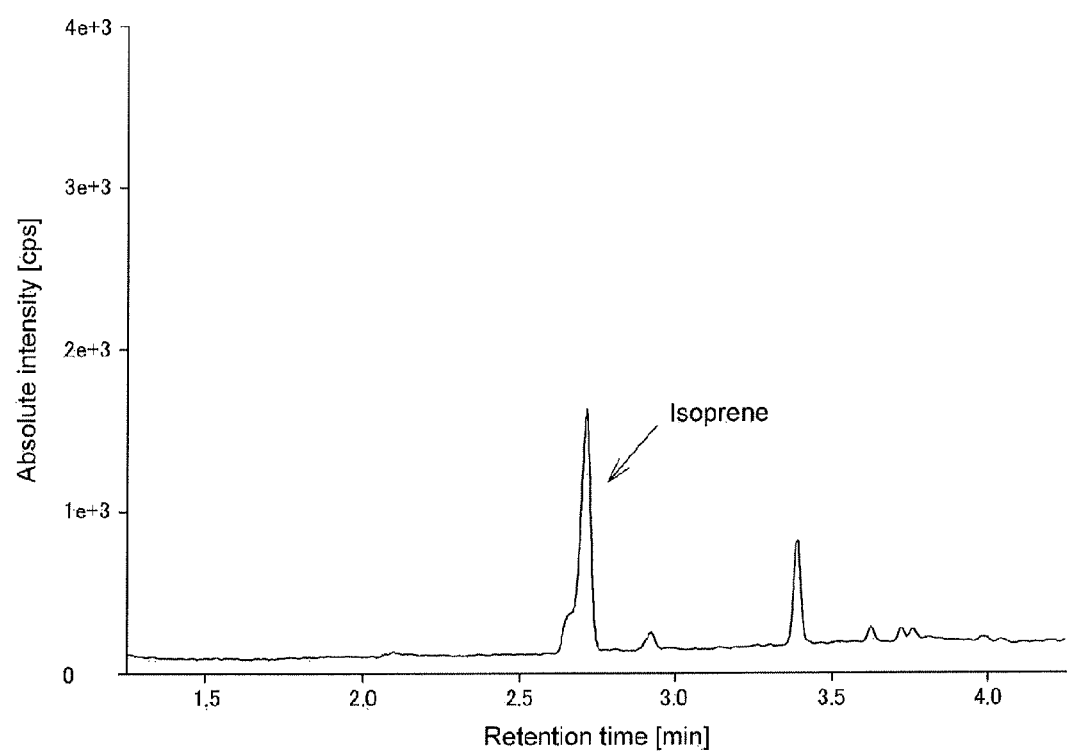
FIG. 6 is a gas chromatogram of a syngas fermentation gas phase component of *C. ljungdahlii* carrying plasmid pSCi::MVA-IspS-idi.

As shown in FIG. 6, it was demonstrated that *C. ljungdahlii* carrying pSCi::MVA-idi-ispS vector generates isoprene.

ATCC medium: Composition of 1754 PETC medium is shown below.

| | |
|---|---|
| NH₄Cl | 1.0 g |
| KCl | 0.1 g |
| MgSO₄·7H₂O | 0.2 g |
| NaCl | 0.8 g |
| KH₂PO₄ | 0.1 g |
| CaCl₂·2H₂O | 20.0 mg |
| Yeast extract | 1.0 g |
| Trace Elements (see below) | 10.0 mL |
| Wolfe's Vitamin Solution (see below) | 10.0 mL |
| NaHCO₃ | 2.0 g |
| Reducing Agent (see below) | 10.0 mL |
| Distilled water | 980.0 mL |
| Final pH 5.9 | |

(Trace Elements)

| | |
|---|---|
| Nitrilotriacetic acid | 2.0 g |
| MnSO₄ H₂O | 1.0 g |
| Fe(SO₄)₂(NH₄)₂·6H₂O | 0.8 g |
| CoCl₂·6H₂O | 0.2 g |
| ZnSO₄·7H₂O | 0.2 mg |
| CuCl₂·2H₂O | 20.0 mg |
| NiCl₂·6H₂O | 20.0 mg |
| Na₂MoO₄·2H₂O | 20.0 mg |
| Na₂SeO₄ | 20.0 mg |
| Na₂WO₄ | 20.0 mg |
| Distilled water | 1.0 L |

(Wolfe's Vitamin Solution)

Available from ATCC as a sterilized ready-to-use solution (Vitamin Supplement, catalog no. MD-VS)

| | |
|---|---|
| Biotin | 2.0 mg |
| Folic acid | 2.0 mg |
| Pyridoxine hydrochloride | 10.0 mg |
| Thiamine·HCl | 5.0 mg |
| Riboflavin | 5.0 mg |
| Nicotinic acid | 5.0 mg |
| Calcium D-(+)-pantothenate | 5.0 mg |
| Vitamin B12 | 0.1 mg |
| p-Aminobenzoic acid | 5.0 mg |
| Thioctic acid | 5.0 mg |
| Distilled water | 1.0 L |

(Reducing Agent)

| | |
|---|---|
| NaOH | 0.9 g |
| L-cysteine·HCl | 4.0 g |
| Na₂S·9H₂O | 4.0 g |
| Distilled water | 100.0 mL |

---

The invention claimed is:

1. A recombinant cell prepared by introducing a nucleic acid encoding isoprene synthase into a host cell wherein the host cell is a *Clostridium* bacterium or a *Moorella* bacterium, wherein the nucleic acid is expressed in the host cell, and the recombinant cell is capable of producing isoprene from at least one C1 compound selected from the group consisting of carbon monoxide and carbon dioxide, wherein a nucleic acid encoding a group of exogenous enzymes acting in a mevalonate pathway is further introduced so that an isopentenyl diphosphate synthesis ability by a mevalonate pathway is further imparted, and wherein the group of exogenous enzymes acting in a mevalonate pathway comprises mevalonate kinase, mevalonate diphosphate decarboxylase, phosphomevalonate kinase, isopentenyl diphosphate (IPP) isomerase, 3-hydroxy-3-methylglutaryl coenzyme A (HMG-CoA) reductase, and HMG-CoA synthase.

2. The recombinant cell according to claim 1, having carbon monoxide dehydrogenase.

3. The recombinant cell according to claim 1, wherein the mevalonate pathway is that of yeast, prokaryote or actinomycete.

4. The recombinant cell according to claim 1, wherein a nucleic acid encoding at least one enzyme acting in a non-mevalonate pathway is further introduced, and the nucleic acid is expressed in the host cell.

5. The recombinant cell according to claim 4, wherein the non-mevalonate pathway is that of other organism than the host cell.

6. The recombinant cell according to claim 1, wherein the isoprene synthase is derived from plant.

7. The recombinant cell according to claim 1, wherein the nucleic acid encoding isoprene synthase encodes the following (a), (b) or (c):
(a) a protein consisting of an amino acid sequence of SEQ ID NO: 2,
(b) a protein consisting of an amino acid sequence in which 1 to 20 amino acids are deleted, substituted or added in the amino acid sequence of SEQ ID NO: 2, and having isoprene synthase activity, and
(c) a protein consisting of an amino acid sequence having a homology of 90% or more with the amino acid sequence of SEQ ID NO: 2, and having isoprene synthase activity.

8. The recombinant cell according to claim 1, wherein the nucleic acid introduced into the host cell is codon-modified.

9. The recombinant cell according to claim 1, wherein the nucleic acid introduced into the host cell is incorporated in a genome of the host cell.

10. The recombinant cell according to claim 1, wherein the nucleic acid introduced into the host cell is incorporated in a plasmid.

11. The recombinant cell according to claim 1, wherein the nucleic acid encoding isoprene synthase and the nucleic acid encoding a group of exogenous enzymes acting in a mevalonate pathway are regulated by a constitutive promoter.

12. A method for producing isoprene by culturing the recombinant cell according to claim 1 using at least one C1 compound selected from the group consisting of carbon monoxide and carbon dioxide as a carbon source, to allow the recombinant cell to produce isoprene.

13. A method for producing isoprene by bringing at least one C1 compound selected from the group consisting of carbon monoxide and carbon dioxide into contact with the recombinant cell according to claim 1, to allow the recombinant cell to produce isoprene from the C1 compound.

14. The method according to claim 12, wherein the recombinant cell is provided with a gas mainly containing carbon monoxide and hydrogen, or a gas mainly containing carbon dioxide and hydrogen.

15. The method according to claim 12, wherein the recombinant cell is prepared from a *Clostridium* bacterium or a *Moorella* bacterium as a host cell, and isoprene released outside the recombinant cell is recovered.

16. The method according to claim 13, wherein the recombinant cell is provided with a gas mainly containing carbon monoxide and hydrogen, or a gas mainly containing carbon dioxide and hydrogen.

17. The method according to claim 13, wherein the recombinant cell is prepared from a *Clostridium* bacterium or a *Moorella* bacterium as a host cell, and isoprene released outside the recombinant cell is recovered.

* * * * *

SEQUENCE LISTING

<160> NUMBER OF SEQ ID NOS: 20

<210> SEQ ID NO 1
<211> LENGTH: 1788
<212> TYPE: DNA
<213> ORGANISM: Populus nigra
<220> FEATURE:
<221> NAME/KEY: CDS
<222> LOCATION: (1)..(1788)
<223> OTHER INFORMATION:

<400> SEQUENCE: 1

```
atg gca act gaa tta ttg tgc ttg cac cgt cca atc tca ctg aca cac      48
Met Ala Thr Glu Leu Leu Cys Leu His Arg Pro Ile Ser Leu Thr His
1               5                   10                  15 aaa ttg ttc aga aat ccc ttg cct aaa gtc atc cag gcc act ccc tta      96
Lys Leu Phe Arg Asn Pro Leu Pro Lys Val Ile Gln Ala Thr Pro Leu
            20                  25                  30 act ttg aaa ctc aga tgt tct gta agc aca gaa aac gtc agc ttc aca     144
Thr Leu Lys Leu Arg Cys Ser Val Ser Thr Glu Asn Val Ser Phe Thr
        35                  40                  45 gaa aca gaa aca gaa acc aga agg tct gcc aat tat gaa cca aat agc     192
Glu Thr Glu Thr Glu Thr Arg Arg Ser Ala Asn Tyr Glu Pro Asn Ser
    50                  55                  60 tgg gat tat gat tat ttg ctg tct tcg gac act gac gaa tcg att gaa     240
Trp Asp Tyr Asp Tyr Leu Leu Ser Ser Asp Thr Asp Glu Ser Ile Glu
65                  70                  75                  80 gta tac aaa gac aag gcc aaa aag ctg gag gct gag gtg aga aga gag     288
Val Tyr Lys Asp Lys Ala Lys Lys Leu Glu Ala Glu Val Arg Arg Glu
                85                  90                  95 att aac aat gaa aag gca gag ttt ttg act ctg cct gaa ctg ata gat     336
Ile Asn Asn Glu Lys Ala Glu Phe Leu Thr Leu Pro Glu Leu Ile Asp
            100                 105                 110 aat gtc caa agg tta gga tta ggt tac cgg ttc gag agt gac ata agg     384
Asn Val Gln Arg Leu Gly Leu Gly Tyr Arg Phe Glu Ser Asp Ile Arg
        115                 120                 125
```

| | | | | | | | | | | | | | | | | |
|---|---|---|---|---|---|---|---|---|---|---|---|---|---|---|---|---|
| aga | gcc | ctt | gat | aga | ttt | gtt | tct | tca | gga | gga | ttt | gat | gct | gtt | aca | 432 |
| Arg | Ala | Leu | Asp | Arg | Phe | Val | Ser | Ser | Gly | Gly | Phe | Asp | Ala | Val | Thr | |
| | 130 | | | | 135 | | | | | 140 | | | | | | |
| aaa | act | agc | ctt | cat | gct | act | gct | ctt | agc | ttc | agg | ctt | ctc | aga | cag | 480 |
| Lys | Thr | Ser | Leu | His | Ala | Thr | Ala | Leu | Ser | Phe | Arg | Leu | Leu | Arg | Gln | |
| 145 | | | | 150 | | | | | 155 | | | | | | 160 | |
| cat | ggc | ttt | gag | gtc | tct | caa | gaa | gcg | ttc | agc | gga | ttc | aag | gat | caa | 528 |
| His | Gly | Phe | Glu | Val | Ser | Gln | Glu | Ala | Phe | Ser | Gly | Phe | Lys | Asp | Gln | |
| | | | | 165 | | | | | 170 | | | | | 175 | | |
| aat | ggc | aat | ttc | ttg | aaa | aac | ctt | aag | gag | gac | atc | aag | gca | ata | cta | 576 |
| Asn | Gly | Asn | Phe | Leu | Lys | Asn | Leu | Lys | Glu | Asp | Ile | Lys | Ala | Ile | Leu | |
| | | | 180 | | | | | 185 | | | | | 190 | | | |
| agc | cta | tat | gaa | gct | tca | ttt | ctt | gcc | tta | gaa | gga | gaa | aat | atc | ttg | 624 |
| Ser | Leu | Tyr | Glu | Ala | Ser | Phe | Leu | Ala | Leu | Glu | Gly | Glu | Asn | Ile | Leu | |
| | | 195 | | | | | 200 | | | | | 205 | | | | |
| gat | gag | gcc | aag | gtg | ttt | gca | ata | tca | cat | cta | aaa | gag | ctc | agc | gaa | 672 |
| Asp | Glu | Ala | Lys | Val | Phe | Ala | Ile | Ser | His | Leu | Lys | Glu | Leu | Ser | Glu | |
| | 210 | | | | 215 | | | | | 220 | | | | | | |
| gaa | aag | att | gga | aaa | gac | ctg | gcc | gaa | cag | gtg | aat | cat | gca | ttg | gag | 720 |
| Glu | Lys | Ile | Gly | Lys | Asp | Leu | Ala | Glu | Gln | Val | Asn | His | Ala | Leu | Glu | |
| 225 | | | | 230 | | | | | 235 | | | | | | 240 | |
| ctt | cca | ttg | cat | cga | agg | acg | caa | aga | cta | gaa | gct | gtt | tgg | agc | att | 768 |
| Leu | Pro | Leu | His | Arg | Arg | Thr | Gln | Arg | Leu | Glu | Ala | Val | Trp | Ser | Ile | |
| | | | | 245 | | | | | 250 | | | | | 255 | | |
| gaa | gca | tac | cgt | aaa | aag | gaa | gat | gca | gat | caa | gta | ctg | cta | gaa | ctt | 816 |
| Glu | Ala | Tyr | Arg | Lys | Lys | Glu | Asp | Ala | Asp | Gln | Val | Leu | Leu | Glu | Leu | |
| | | | 260 | | | | | 265 | | | | | 270 | | | |
| gct | ata | ttg | gac | tac | aac | atg | att | caa | tca | gta | tac | caa | aga | gat | ctt | 864 |
| Ala | Ile | Leu | Asp | Tyr | Asn | Met | Ile | Gln | Ser | Val | Tyr | Gln | Arg | Asp | Leu | |
| | | 275 | | | | | 280 | | | | | 285 | | | | |
| cgc | gag | aca | tca | agg | tgg | tgg | agg | cgt | gtg | ggt | ctt | gca | aca | aag | ttg | 912 |
| Arg | Glu | Thr | Ser | Arg | Trp | Trp | Arg | Arg | Val | Gly | Leu | Ala | Thr | Lys | Leu | |
| | 290 | | | | 295 | | | | | 300 | | | | | | |
| cat | ttt | gct | aga | gac | agg | tta | att | gaa | agc | ttt | tac | tgg | gca | gtt | gga | 960 |
| His | Phe | Ala | Arg | Asp | Arg | Leu | Ile | Glu | Ser | Phe | Tyr | Trp | Ala | Val | Gly | |
| 305 | | | | 310 | | | | | 315 | | | | | | 320 | |
| gtt | gcg | ttt | gaa | cct | caa | tac | agt | gat | tgc | cgt | aat | tcc | gta | gca | aaa | 1008 |
| Val | Ala | Phe | Glu | Pro | Gln | Tyr | Ser | Asp | Cys | Arg | Asn | Ser | Val | Ala | Lys | |
| | | | | 325 | | | | | 330 | | | | | 335 | | |
| atg | ttt | tcg | ttt | gta | aca | atc | att | gat | gat | atc | tat | gat | gtt | tat | ggt | 1056 |
| Met | Phe | Ser | Phe | Val | Thr | Ile | Ile | Asp | Asp | Ile | Tyr | Asp | Val | Tyr | Gly | |
| | | | 340 | | | | | 345 | | | | | 350 | | | |
| act | ctg | gat | gag | ttg | gag | cta | ttt | aca | gat | gct | gtt | gag | aga | tgg | gat | 1104 |
| Thr | Leu | Asp | Glu | Leu | Glu | Leu | Phe | Thr | Asp | Ala | Val | Glu | Arg | Trp | Asp | |
| | | 355 | | | | | 360 | | | | | 365 | | | | |
| gtt | aat | gcc | atc | gat | gat | ctt | ccg | gat | tat | atg | aag | ctc | tgc | ttc | cta | 1152 |
| Val | Asn | Ala | Ile | Asp | Asp | Leu | Pro | Asp | Tyr | Met | Lys | Leu | Cys | Phe | Leu | |
| | 370 | | | | 375 | | | | | 380 | | | | | | |
| gct | ctc | tat | aac | act | atc | aat | gag | ata | gct | tat | gat | aat | ctg | aag | gac | 1200 |
| Ala | Leu | Tyr | Asn | Thr | Ile | Asn | Glu | Ile | Ala | Tyr | Asp | Asn | Leu | Lys | Asp | |
| 385 | | | | 390 | | | | | 395 | | | | | | 400 | |
| aag | ggg | gaa | aac | att | ctt | cca | tac | cta | aca | aaa | gcg | tgg | gca | gat | tta | 1248 |
| Lys | Gly | Glu | Asn | Ile | Leu | Pro | Tyr | Leu | Thr | Lys | Ala | Trp | Ala | Asp | Leu | |
| | | | | 405 | | | | | 410 | | | | | 415 | | |
| tgc | aat | gca | ttc | cta | caa | gaa | gca | aaa | tgg | ttg | tac | aat | aag | tcc | aca | 1296 |
| Cys | Asn | Ala | Phe | Leu | Gln | Glu | Ala | Lys | Trp | Leu | Tyr | Asn | Lys | Ser | Thr | |
| | | | 420 | | | | | 425 | | | | | 430 | | | |
| cca | aca | ttt | gat | gaa | tat | ttc | gga | aat | gca | tgg | aaa | tca | tcc | tca | ggg | 1344 |
| Pro | Thr | Phe | Asp | Glu | Tyr | Phe | Gly | Asn | Ala | Trp | Lys | Ser | Ser | Ser | Gly | |

```
                435                 440                 445
cct ctt caa cta gtt ttt gcc tac ttt gcc gtt gtt caa aac atc aag       1392
Pro Leu Gln Leu Val Phe Ala Tyr Phe Ala Val Val Gln Asn Ile Lys
    450                 455                 460 aaa gag gaa att gat aac tta caa aag tat cat gat atc atc agt agg       1440
Lys Glu Glu Ile Asp Asn Leu Gln Lys Tyr His Asp Ile Ile Ser Arg
465                 470                 475                 480 cct tcc cac atc ttt cgt ctt tgc aac gac ttg gct tca gca tcg gct       1488
Pro Ser His Ile Phe Arg Leu Cys Asn Asp Leu Ala Ser Ala Ser Ala
                485                 490                 495 gag ata gcg aga ggt gaa acc gcg aat tct gta tca tgc tac atg cgt       1536
Glu Ile Ala Arg Gly Glu Thr Ala Asn Ser Val Ser Cys Tyr Met Arg
            500                 505                 510 aca aaa ggc att tct gag gaa ctt gct act gaa tcc gta atg aat ttg       1584
Thr Lys Gly Ile Ser Glu Glu Leu Ala Thr Glu Ser Val Met Asn Leu
        515                 520                 525 atc gac gaa acc tgg aaa aag atg aac aaa gaa aag ctt ggt ggc tct       1632
Ile Asp Glu Thr Trp Lys Lys Met Asn Lys Glu Lys Leu Gly Gly Ser
530                 535                 540 ctg ttt gca aaa cct ttt gtc gaa aca gct att aac ctt gca cga caa       1680
Leu Phe Ala Lys Pro Phe Val Glu Thr Ala Ile Asn Leu Ala Arg Gln
545                 550                 555                 560 tcc cat tgc act tat cac aac gga gat gcg cat act tca cca gat gag       1728
Ser His Cys Thr Tyr His Asn Gly Asp Ala His Thr Ser Pro Asp Glu
                565                 570                 575 ctc act agg aaa cgt gtc ctg tca gta atc aca gag cct att cta ccc       1776
Leu Thr Arg Lys Arg Val Leu Ser Val Ile Thr Glu Pro Ile Leu Pro
            580                 585                 590 ttt gag aga taa                                                        1788
Phe Glu Arg
        595

<210> SEQ ID NO 2
<211> LENGTH: 595
<212> TYPE: PRT
<213> ORGANISM: Populus nigra

<400> SEQUENCE: 2

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Thr Arg Arg Ser Ala Asn Tyr Glu Pro Asn Ser
    50                  55                  60

Trp Asp Tyr Asp Tyr Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Pro Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Ala Val Thr
    130                 135                 140

Lys Thr Ser Leu His Ala Thr Ala Leu Ser Phe Arg Leu Leu Arg Gln
145                 150                 155                 160
```

-continued

His Gly Phe Glu Val Ser Gln Glu Ala Phe Ser Gly Phe Lys Asp Gln
                165                 170                 175

Asn Gly Asn Phe Leu Lys Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Asp Leu Ala Glu Gln Val Asn His Ala Leu Glu
225                 230                 235                 240

Leu Pro Leu His Arg Arg Thr Gln Arg Leu Ala Val Trp Ser Ile
                245                 250                 255

Glu Ala Tyr Arg Lys Lys Glu Asp Ala Asp Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asp Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Glu Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
    450                 455                 460

Lys Glu Glu Ile Asp Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Trp Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

```
Leu Thr Arg Lys Arg Val Leu Ser Val Ile Thr Glu Pro Ile Leu Pro
            580                 585                 590

Phe Glu Arg
        595

<210> SEQ ID NO 3
<211> LENGTH: 59
<212> TYPE: DNA
<213> ORGANISM: Artificial
<220> FEATURE:
<223> OTHER INFORMATION: oligonucleotide primer for PCR

<400> SEQUENCE: 3
ggccgcggat ccagaattta aaaggaggga ttaaaatggc aactgaatta ttgtgcttg       59

<210> SEQ ID NO 4
<211> LENGTH: 84
<212> TYPE: DNA
<213> ORGANISM: Artificial
<220> FEATURE:
<223> OTHER INFORMATION: oligonucleotide primer for PCR

<400> SEQUENCE: 4
ccgcgccgga tccgacatta aaaaaataag agttaccatt taaggtaact cttattttta     60
ttatctctca aagggtagaa tagg                                            84

<210> SEQ ID NO 5
<211> LENGTH: 32
<212> TYPE: DNA
<213> ORGANISM: Artificial
<220> FEATURE:
<223> OTHER INFORMATION: oligonucleotide linker

<400> SEQUENCE: 5
gatcgctgca ggtttaaacg gatccactac cg                                   32

<210> SEQ ID NO 6
<211> LENGTH: 32
<212> TYPE: DNA
<213> ORGANISM: Artificial
<220> FEATURE:
<223> OTHER INFORMATION: oligonucleotide linker

<400> SEQUENCE: 6
aattcggtag tggatccgtt taaacctgca gc                                   32

<210> SEQ ID NO 7
<211> LENGTH: 131
<212> TYPE: DNA
<213> ORGANISM: Artificial
<220> FEATURE:
<223> OTHER INFORMATION: oligonucleotide linker

<400> SEQUENCE: 7 gttttttaaca aaatatattg ataaaaataa taatagtggg tataattaag ttgttagaga    60
aaacgtataa attagggata aactatggaa cttatgaaat agattgaaat ggtttatctg    120
ttaccccgta g                                                         131

<210> SEQ ID NO 8
<211> LENGTH: 139
<212> TYPE: DNA
<213> ORGANISM: Artificial
<220> FEATURE:
<223> OTHER INFORMATION: oligonucleotide linker
```

<400> SEQUENCE: 8

```
gatcctacgg ggtaacagat aaaccatttc aatctatttc ataagttcca tagtttatcc      60
ctaatttata cgttttctct aacaacttaa ttatacccac tattattatt tttatcaata     120
tattttgtta aaaactgca                                                   139
```

<210> SEQ ID NO 9
<211> LENGTH: 6441
<212> TYPE: DNA
<213> ORGANISM: Streptomyces griseolosporeus

<400> SEQUENCE: 9

```
gttgactctt ccgacctcgg tggaggaggg atcgaaggcc caccgggctc gcgccgtcgg      60
caccggtcgc gctcatgcca aggccattct gctgggagag cacgcggtcg tgtacgaac     120
cccggcgctc gcgatgccca ttccccaact cgcggtcacg gcaagcgccg gctggtccgg    180
ccgatccgcc gagagccggg gcggtccgac cttccacatg accgggtcgg cttcccgcgc    240
ggtcacggca caggccttgg acggtctgcg acgtctgacc gcctcggtca aggcgcacac    300
gggagtgacc gacggacaac acctcgacgt cagcctcgac ggggcgattc cgcccggccg    360
cgggctcggc tccagcgccg cgaacgcacg agcgatcatc ctcgccctgg ccgacctctt    420
cggccgggag ctgaccgagg gcgaggtgtt cgacctggtg caggaggccg agaacctgac    480
gcacggccgg gccagcggcg tcgacgccgt gaccgtcggc gccaccgccc cgctcctctt    540
ccgggcgggc acggcacagg cgctggacat cggctgcgac gcactgttcg tcgtcgcgga    600
cagcggaacc gcagggagca ccaaggaggc gatcgagctg cttcgcgccg gattccgggc    660
cggggccgga aaggaggaac ggttcatgca ccgtgccgcg cacctcgtcg acgatgccag    720
ggcctccctc gccgagggcg aacccgaggc gttcggatcg tgcctgaccg agtatcacgg    780
cctgctgcgc ggggcgggtc tgagcaccga ccggatcgat gcactggtgg atgccgcgct    840
gcaggccgac agcctgggcg ccaagatcac cggtggcggt ctgggcggtt gtgttctcgc    900
gatgtcccgc ccggagcggg ccgaggaagt ggcccggcag ctgcacgccg ccggcgccgt    960
acgcacgtgg gccgtacagc tgaggaggtc cactcatgag cgctgaacag ccgtcaaccc   1020
tgctgtccgc gccgcgacgg acaccgcgac agccgttgcc cagccgaaca tcgcgctgat   1080
caagtactgg ggcaagaagg acgagcacct ggtcctgccc cgtaccgaca gcctgtcgat   1140
gactctggac atcttcccga cgaccacccg ggtccagctc gcgcccggcg ccgggcagga   1200
cacggtggcc ttcaacggcg agcccgcgac gggagaggcc gagcggcgca tcaccgcatt   1260
cctccggctg gtgcgggagc ggtcggggcg caccgaacgg gcccgcgtcg agacggagaa   1320
caccgtcccc accggggccg gcctggcctc gtcggccagc ggtttcgctg ccctcgccgt   1380
cgccgccgcc gcggcgtacg ggctcggtct cgacgcgcgg ggcctgtccc ggctggcccg   1440
acgcggctcc gggtcggcct cccggtcgat cttcgacggg ttcgccgtgt ggcacgccgg   1500
ccacgccggc ggcactcccg aggaggccga tctcggctcg tacgccgaac cggtgccggc   1560
cgtggacctg gagccggcgc tggtggtcgc ggtggtcagc gccgcccca aggcggtgtc   1620
cagccgggag gccatgcgga ggaccgtgga cacctcaccg ctgtacgagc cgtgggcggt   1680
gtccagccgg gccgacctgg cggacatcgg agccgcgctc gcccgcggca acctgccggc   1740
ggtgggcgag atcgcggagc gcaacgcct cggcatgcac gccaccatgc tggccgcacg   1800
ccccgccgtg cgctacctgt caccggcctc gctcgccgtg ctcgacggcg ttctgcagtt   1860
```

```
gcggcgggac ggcgtgccgg cctacgcgac gatggacgcc ggtcccaacg tgaaggtgct    1920
ctgcccgcgt tcggacgccg agcgggtcgc ggaagccctg cgccgccgcc cgccggtcgg    1980
agcggtgcac atcgccggtc cggggcgggg tgcccgcctg gtggcggagg aatgccggtg    2040
accgccccgc gcgcggtgac ccggcgcgcc cgggcaagc tcttcgtcgc gggtgaatac     2100
gcggtggtgg aaccgggcaa ccgggcgatc ctggtggcag tcgaccggta cgtcaccgtc    2160
accgtgtccg acgcgccgc acccgtgtc gtcgtctcct ccgacatcgg agccggcccg      2220
gtgcaccacc cgtggcagga cgggcggctg acaggcggta cgggcacacc tcatgtggtg    2280
gcggcggtcg agaccgtggc ccgcctcctg gccgaacgcg gccggtccgt cccgccgttg    2340
gggtggtcga tcagcagcac gctgcacgag gacggccgga agttcggact gggctccagc    2400
ggcgcggtga cggtggcgac ggtcagtgcc gtcgcagccc attgcggact ggaactcacc    2460
gccgaagaac gcttccggac ggcgctgatc gcctccgccc gcatcgaccc caggggatcc    2520
ggcggagaca tcgccaccag cacctggggc ggctggatcg cctaccgggc gcccgaccgg    2580
gacgccgtac tcgacttgac ccgccgtcag ggggtcgacg aggcactccg ggcgccgtgg    2640
ccgggcttct ccgtacgact gtcgccgccc cggaacctct gcctcgaggt cggctggacc    2700
ggcaaccccg tgtccaccac gtccctcctg acggacctgc atcggcgcac ctggcggggc    2760
agccccgcgt accggaggta cgtcggggcg accggcgagc tcgtggacgc cgcagtcatc    2820
gcgctggagg acgcgacac cgagggcctg ttgcggcagg tccggcgggc ccgtcacgag     2880
atggtccgcc tcgacgacga ggtcggcctc ggcatcttca ccccgaact gacggccctc     2940 tgcgccatcg ccgaacgcgc cggcgcgcc aagcccgcgg gggccggggg cggcgactgc    3000
ggcatcgcgc tgctggacgc cgaggcccgc tacgaccgct caccgttgca ccggcaatgg    3060
gccgcggccg gggtgctgcc gctactggtg tcgcctgcca cggaaggagt cgaggaatga    3120
gcagtgccca gcgcaaggac gaccatgtcc ggctcgccac ggagcagcag cgcgcgcaca    3180
gcggacgcaa ccagttcgac gacgtgtcgt tcgtccacca cgccctcgcc ggaatcgacc    3240
ggccggacgt ccgcctggcc acgacgttcg ccggcatcac ctggcgactg ccgctgtaca    3300
tcaacgcgat gacgggcggc agcgccaaga ccggcgccat caaccgggac ctggccgtcg    3360
ccgccaggga gaccggcgcc gccatcgcgt ccgggtccat gcacgccttt ttcagggacc    3420
cctcctgcgc ggacaccttc gcgtgctgc gcaccgagaa ccccgacggt ttcgtgatgg     3480
cgaacgtcaa cgcgaccgcg tccgtcgaca acgcccgccg ggccgtcgac ctgatcgagg    3540
cgaacgccct gcagatccac ctgaacacgg cgcaggagac gcccatgccg gagggcgacc    3600
ggtcgttcgg gtcgtggccg gcccagatcg cgaagatcac ggcggccgtc gacgtcccgg    3660
tgatcgtcaa ggaggtcggc aacgggctca gcaggcagac cctcctggcg ctgccggatc    3720 tggggggtccg ggtcgccgac gtcagcggcc gcggcggcac cgacttcgcc gtatcgaga    3780 acagccggcg ccccctgggc gactacgcct tcctgcacgg ctggggggcag tccaccccgg   3840 cctgtctgct ggacgctcag gacgtcggct tcccctgct ggcctccggt gggatccgca    3900
acccgctcga cgtcgcccgg gcgctcgcgc tcggcgccgg cgccgtgggc tcctcgggcg    3960
tattcctgcg cacgctgatc gacgggggcg tatccgccct ggtcgcacag atctccacct   4020
ggctggacca gctcgccgcg ctgcagacca tgctcggtgc gcggaccccc gccgacctca   4080
cccgctgcga cgtgctgatc cacggccgc tccggtcctt ctgcacggac cggggcatag    4140
acatcgggcg gttcgcccgg cgcagcagct ccgccgacat ccgttccgag atgacaggaa    4200
gcacacgatg accgaagcgc acgccaccgc cggcgtcccg atgcggtggg tggggcccgt    4260
```

-continued

```
ccgcatctcg ggaaacgtcg ccaccatcga acccaggtg ccgctggcca cgtacgagtc      4320
tccgctctgg ccttcggtgg gccgcggcgc gaaggtgtcc cggctgaccg agaagggcat      4380
cgtcgccacg ctcgtcgacg agcgcatgac ccgttccgtg ctcgtcgagg cgaccgacgc      4440
gctcaccgcg ctctccgcgg cacgaccat cgaggcccgc atcgacgagc tgcgcgagct       4500
ggtgcgcggc tgcagccggt tcgcccagct gatcggcatc cggcacgaga tcaccggaaa      4560
cctgctgttc gtccggttcg agttcagcac cggtgacgcc tccggcaca acatggcgac       4620 cctggcttcc gacgtgctcc tccagcatct gctggaaacg gttcccggca tctcctacgg      4680
gtcgatctcc gggaactact gcacggacaa gaaggccacc gccatcaacg gcatcctggg      4740
ccgcggcaag aacgtcgtca ccgagctgct cgtgccgcgt gacgtggtgg ccgacgtcct      4800
gaacaccacc gccgcgaaga tcgccgagct gaacctccgc aagaacctgc tcgggacact      4860
tctcgcaggc ggcatccggt cggcgaacgc ccactacgcg aacatgctgc tcgcgttcta      4920
cctggcgacc ggtcaggacg cggcgaacat cgtcgagggc tcccagggcg tcgtcacggc      4980
cgaggaccgc gacggcgacc tctacttagc ctgcacactg ccgaacctca tcgtcggcac      5040
ggttggcaac ggcaagggcc tgggcttcgt ggagaccaac ctgaaccggc tcggctgccg      5100
tgcggaccgc gagcccggcg agaacgcccg ccggctcgcc gtcatcgcgg cggccacggt      5160
gctctgcggg gagctgtcgc tgctcgcggc gcagaccaac cccggcgaac tgatgcgtgc      5220
gcatgtccaa ctggaacgag gccacacgac cgcgaaggct ggtgtctaga gcatgcccct      5280
cgccataggc atccatgatc tgtcgttcgc caccggcgag ttcggctgcc gcacaccgcc      5340
ctcgccgctc acaacggaac cgagatcggc aagtaccacg cggcatcgg ccaggagtcg       5400 atgagcgtcc cggccgccga cgaggacatc gtgaccctgg ccgcgacggc tgccgcaccg      5460
atcgtcgccc ggcacggcag cgaccggatc cgcacggtcg tgctcgcgac cgaatcgtcg      5520
atcgaccagg cgaagtcggc cggtgtgtac gtccactccc tgctcggact gccgtcggcc      5580
acccgcgtcg tggagctgaa gcaggcctgt tacggggcca cggccggcct gcagttcgcc      5640
atcggtctgg tgcagcgcga ccccgcccag caggttctcg tcatcgccag tgacgtctcc      5700
aagtacgacc tggacagccc cggtgaggcg acgcaggggcg ccgccgcggt cgccatgctc      5760
gtaggcgccg atccggggct ggtgcggatc gaggatccgt cgggcctgtt caccgtcgac      5820
gtcatggact tctggcggcc gaactaccgc accacggctc tggtcgacgg ccaggaatcc      5880
atcggcgcct acctccaggc ggtggagggg gcctggaagg actactcgga gcggggcggc      5940
cactccctga gcagttcgc cgcgttctgc taccaccagc cgttcaccaa gatggctcac       6000
aaggcccacc ggcacctgct gaactactgc agccacgaca tccaccacga cgacgtcacg      6060
cgtgccgtcg gccggaccac cgcctacaac agggtgatcg ggaacagcta caccgcgtcc      6120
gtctacctgg gcctcgccgc gctcctcgac caggccgacg acctgaccgg tgagcgcatc      6180
ggattcctca gctacggttc cggcagcgtc gccgagttct tcggcgggat cgtcgtcgcc      6240
ggataccggg accggctgcg gacggcggcg aacatcgagg ccgtctcccg gcgacggccc      6300
atcgactacg ccggctaccg cgagctgcac gagtgggcct tccccgcccg acggggagcc      6360
cactccaccc cgcagcagac cacgggaccg ttccggctgt ccggtatcag cggccacaag      6420
cgcctctacc gagcgtgctg a                                                6441
```

<210> SEQ ID NO 10
<211> LENGTH: 62
<212> TYPE: DNA

<213> ORGANISM: Artificial
<220> FEATURE:
<223> OTHER INFORMATION: oligonucleotide primer for PCR

<400> SEQUENCE: 10
cgggtaccaa ttttgttaat aattcaggga gggattctaa atgactcttc cgacctcggt    60
gg    62

<210> SEQ ID NO 11
<211> LENGTH: 71
<212> TYPE: DNA
<213> ORGANISM: Artificial
<220> FEATURE:
<223> OTHER INFORMATION: oligonucleotide primer for PCR

<400> SEQUENCE: 11
aggtaccatt aaaaaaataa gagttaccat ttaaggtaac tcttattttt atcagcacgc    60
tcggtagagg c    71

<210> SEQ ID NO 12
<211> LENGTH: 39
<212> TYPE: DNA
<213> ORGANISM: Artificial
<220> FEATURE:
<223> OTHER INFORMATION: oligonucleotide primer for PCR

<400> SEQUENCE: 12
tggtacctta ttcttttatc tctcaaaggg tagaatagg    39

<210> SEQ ID NO 13
<211> LENGTH: 15
<212> TYPE: DNA
<213> ORGANISM: Artificial
<220> FEATURE:
<223> OTHER INFORMATION: oligonucleotide linker

<400> SEQUENCE: 13
gatccggtac ctttg    15

<210> SEQ ID NO 14
<211> LENGTH: 15
<212> TYPE: DNA
<213> ORGANISM: Artificial
<220> FEATURE:
<223> OTHER INFORMATION: oligonucleotide linker

<400> SEQUENCE: 14
aattcaaagg taccg    15

<210> SEQ ID NO 15
<211> LENGTH: 2620
<212> TYPE: DNA
<213> ORGANISM: Artificial
<220> FEATURE:
<223> OTHER INFORMATION: Designed polynucleotide containing Isopentenyl
      diphosphate isomerase gene and isoprene synthase gene

<400> SEQUENCE: 15
ctgcagtttt taacaaaata tattgataaa aataataata gtgggtataa ttaagttgtt    60
agagaaaacg tataaattag ggataaacta tggaacttat gaaatagatt gaaatggttt   120
atctgttacc ccgtaggatc gagaatttaa aaggagggat aaaatgcaa actgaacatg   180 ttattttatt gaatgcacag ggagttccta ctggtactct ggaaaagtat gccgcacata   240

-continued

```
cagcagacac ccgcttacat ctcgctttct ccagttggct gtttaatgcc aaaggacaat      300
tattagttac cagaagagca ctgagcaaaa aagcatggcc tggcgtgtgg actaactctg      360
tttgtgggca tccacaactg ggagaaagca acgaagacgc agtgatcaga agatgtcgtt     420
atgagcttgg cgtggaaatt actcctcctg aatctatcta tcctgacttt agatacagag      480
ccaccgatcc tagtggcatt gtggaaaatg aagtgtgtcc tgtatttgcc gcaagaacca      540
ctagtgcatt acagatcaat gatgatgaag tgatggatta tcaatggtgt gatttagcag      600
atgtattaca tggtattgat gccactcctt gggctttcag tccttggatg gtgatgcagg      660
caacaaatag agaagccaga aaagattat ctgcatttac ccagcttaaa taattaataa      720
ttaattcgaa cagaaaaaat aagtatttat ataacggtta attgtaagga gggttttta      780 tggcaactga attattgtgt ttgcatagac caatctcact gacacataaa ttgttcagaa      840
atcctttgcc taaagttatc caggccactc ctttaacttt gaacttaga tgttctgtaa      900 gcacagaaaa cgtaagcttc acagaaacag aaacagaaac cagaaggtct gccaattatg      960
aaccaaatag ctgggattat gattatttgc tgtcttctga cactgacgaa tctattgaag     1020
tatacaaaga caaggccaaa aagctggagg ctgaggtgag aagagagatt aacaatgaaa     1080
aggcagagtt tttgactctg cctgaactga tagataatgt tcaaaggtta ggattaggtt     1140
acagattcga gagtgacata aggagagccc ttgatagatt tgtttcttca ggaggatttg     1200
atgctgttac aaaaactagc cttcatgcta ctgctcttag cttcaggctt ctcagacagc     1260
atggctttga ggtatctcaa gaagctttca gcggattcaa ggatcaaaat ggcaatttct     1320
tgaaaaacct taaggaggac atcaaggcaa tactaagcct atatgaagct tcatttcttg     1380
ccttagaagg agaaaatatc ttggatgagg ccaaggtgtt tgcaatatca catctaaaag     1440
agcttagcga agaaaagatt ggaaaagacc tggccgaaca ggtgaatcat gcattggagc     1500
ttccattgca tagaaggaca caaagactag aagctgtttg gagcattgaa gcatacagaa     1560
aaaaggaaga tgcagatcaa gtactgctag aacttgctat attggactac aacatgattc     1620
aatcagtata ccaaagagat cttagagaga catcaaggtg gtggaggaga gtgggtcttg     1680
caacaaagtt gcattttgct agagacaggt taattgaaag cttttactgg gcagttggag     1740
ttgcatttga acctcaatac agtgattgta gaaattccgt agcaaaaatg tttctttttg     1800
taacaatcat tgatgatatc tatgatgttt atggtactct ggatgagttg gagctattta     1860
cagatgctgt tgagagatgg gatgttaatg ccatcgatga tcttcctgat tatatgaagc     1920 tttgttttcct agctctttat aacactatca atgagatagc ttatgataat ctgaaggaca     1980 aggggggaaaa cattcttcca tacctaacaa agcatgggc agatttatgt aatgcattcc     2040
tacaagaagc aaaatggttg tacaataagt ccacaccaac atttgatgaa tatttcggaa     2100
atgcatggaa atcatcctca gggcctcttc aactagtttt tgcctacttt gccgttgttc     2160
aaaacatcaa gaaagaggaa attgataact acaaaagta tcatgatatc atcagtaggc     2220
cttcccatat ctttagactt tgtaacgact tggcttcagc atctgctgag atagcaagag     2280
gtgaaaccgc aaattctgta tcatgttaca tgagaacaaa aggcatttct gaggaacttg     2340
ctactgaatc cgtaatgaat ttgatcgacg aaacctggaa aaagatgaac aaagaaaagc     2400
ttggtggctc tctgtttgca aaacctttg ttgaaacagc tattaacctt gcaagacaat     2460
cccattgtac ttatcataac ggagatgcac atacttcacc agatgagctt actaggaaaa     2520
gagtactgtc agtaatcaca gagccctatt caccttttga gagataataa aaataagagt     2580
taccttaaat ggtaactctt atttttttaa tgtcggatcc                            2620
```

<210> SEQ ID NO 16
<211> LENGTH: 549
<212> TYPE: DNA
<213> ORGANISM: Escherichia coli

<400> SEQUENCE: 16

| | | | | | |
|---|---|---|---|---|---|
| atgcaaacgg | aacacgtcat | tttattgaat | gcacagggag | ttcccacggg | tacgctggaa | 60 |
| aagtatgccg | cacacacggc | agacacccgc | ttacatctcg | cgttctccag | ttggctgttt | 120 |
| aatgccaaag | acaattatt | agttacccgc | cgcgcactga | gcaaaaaagc | atggcctggc | 180 |
| gtgtggacta | actcggtttg | tgggcaccca | caactgggag | aaagcaacga | agacgcagtg | 240 |
| atccgccgtt | gccgttatga | gcttggcgtg | gaaattacgc | ctcctgaatc | tatctatcct | 300 |
| gactttcgct | accgcgccac | cgatccgagt | ggcattgtgg | aaaatgaagt | gtgtccggta | 360 |
| tttgccgcac | gcaccactag | tgcgttacag | atcaatgatg | atgaagtgat | ggattatcaa | 420 |
| tggtgtgatt | tagcagatgt | attacacggt | attgatgcca | cgccgtgggc | gttcagtccg | 480 |
| tggatggtga | tgcaggcgac | aaatcgcgaa | gccagaaaac | gattatctgc | atttacccag | 540 |
| cttaaataa | | | | | 549 |

<210> SEQ ID NO 17
<211> LENGTH: 2545
<212> TYPE: DNA
<213> ORGANISM: Artificial
<220> FEATURE:
<223> OTHER INFORMATION: Designed polynucleotide containing Isopentenyl
      diphosphate isomer ase gene and isoprene synthase gene

<400> SEQUENCE: 17

| | | | | | |
|---|---|---|---|---|---|
| atgacagcag | ataacaattc | tatgccacat | ggagcagttt | caagttatgc | gaaattagtt | 60 |
| cagaaccaaa | ctccagaaga | catactagag | gaatttccag | aaatcatacc | cttacaacaa | 120 |
| agaccaaata | caagaagttc | ggaaacatct | aatgatgaat | caggtgaaac | ttgttttca | 180 |
| ggacatgatg | aagaacagat | caaactcatg | aacgagaatt | gtattgttct | tgattgggac | 240 |
| gataatgcta | taggtgctgg | tactaaaaag | gtttgtcact | aatggaaaa | tatcgaaaag | 300 |
| ggattgttac | acagagcatt | tagtgtattt | atctttaatg | aacaaggaga | attactactt | 360 |
| caacaaagag | ctacagaaaa | gataacgttt | cctgatttat | ggaccaatac | ttgttgtagt | 420 |
| catcctctat | gtatagatga | tgagttagga | cttaaaggca | aattagacga | caaaatcaaa | 480 |
| ggtgctataa | cagcagctgt | aagaaagtta | gatcatgagt | taggaatacc | tgaagatgag | 540 |
| actaaaacta | gaggaaaatt | ccattttctt | aaccgtatcc | attatatggc | accttctaat | 600 |
| gaaccttggg | gtgaacatga | aatcgattat | atcttgttct | acaaaatcaa | tgctaaggaa | 660 |
| aatcttactg | tgaatcccaa | tgtaaatgaa | gtaagagatt | ttaagtgggt | tagtcctaat | 720 |
| gatctgaaaa | ccatgtttgc | agatcccttc | ctataaattta | caccttggtt | taagattata | 780 |
| tgcgagaatt | atctctttaa | ttggtgggaa | caattggatg | atttgagtga | agttgagaat | 840 |
| gacagacaaa | tacatcgaat | gttatagtag | tgataccgtt | taaacaggaa | gaatcataga | 900 |
| ggaggaatca | atggaagcga | gacgcagtgc | caattatgaa | ccaaatagct | gggattatga | 960 |
| ttatcttctg | agtagtgata | ccgatgaaag | cattgaagta | tataaagata | agccaaaaa | 1020 |
| attagaagca | gaagtgagac | gtgaaattaa | taatgaaaaa | gctgaatttc | tgacactgtt | 1080 |
| agaacttatt | gataatgtgc | agcgcctggg | attaggctat | agatttgaaa | gcgatattag | 1140 |
| aggcgcactg | gatcgttttg | tgagttcagg | tggatttgat | gctgttacaa | aaactagcct | 1200 |

-continued

| | |
|---|---|
| tcatggaact gcgctgagtt ttcgccttct gagacagcac ggctttgaag ttagccaaga | 1260 |
| agcctttagt ggttttaaag atcaaaatgg aaattttctg gaaatcttta aagaagatat | 1320 |
| taaagcaata ctttcactgt atgaagcaag ttttctggca cttgaaggag aaaatatact | 1380 |
| tgatgaagct aaagtttttg cgatttcaca tcttaaagaa ctgtctgaag aaaaaattgg | 1440 |
| caaagaactg gctgaacagg ttaatcatgc gctggaatta ccgcttcacc gcagaaccca | 1500 |
| aagattagaa gccgtttggt ctattgaagc atatcgtaaa aaagaagatg ccaatcaggt | 1560 |
| acttcttgaa ttagcaatac ttgattataa tatgattcag agcgtgtatc aacgtgatct | 1620 |
| tcgcgaaacc agtagatggt ggcgtcgcgt tggccttgct acgaaactgc attttgcgag | 1680 |
| agatcgtctg attgaaagct tttattgggc cgtgggtgtt gcatttgaac cacaatatag | 1740 |
| cgattgtcgt aatagtgttg caaaaatgtt tagttttgta actataattg atgatattta | 1800 |
| tgatgtttat ggtacacttg atgaactgga acttttttact gatgctgtag aacgctggga | 1860 |
| tgtgaatgcg attaatgatc tgccagatta tatgaaactt tgttttcttg ccctgtataa | 1920 |
| tacaattaat gaaattgcat atgataatct taaagataaa ggagaaaata tactgcctta | 1980 |
| tttaactaaa gcatgggctg atttatgcaa tgcttttctt caggaagcga atggctgta | 2040 |
| taataaatca accccctacgt ttgatgatta ttttggcaat gcttggaaat ctagcagtgg | 2100 |
| tccgttacag cttgttttg cttatttgc ggttgtacaa atattaaaa aagaagaaat | 2160 |
| tgaaaatctg caaaaatatc atgatactat ttcacgtcct tctcacatat ttcgcttatg | 2220 |
| taatgatctt gcgtcagcaa gtgcagaaat tgcccgcggt gaaaccgcaa atagcgtaag | 2280 |
| ttgctatatg agaacaaaag gaatttcaga agaacttgca actgaatctg tgatgaatct | 2340 |
| gattgatgaa acctggaaga aaatgaataa agaaaaatta ggcggttctc tgtttgctaa | 2400 |
| accatttgta gaaacggcta taaatcttgc gcgtcagtca cattgcacct atcacaatgg | 2460 |
| agatgcgcat acgtctccgg atgaacttac cagaaaaaga gtgctgagtg tgattaccga | 2520 |
| accgatactg ccatttgaac gctaa | 2545 |

<210> SEQ ID NO 18
<211> LENGTH: 9237
<212> TYPE: DNA
<213> ORGANISM: Artificial
<220> FEATURE:
<223> OTHER INFORMATION: Escherichia coli/Clostridium shuttle vector
      pSCi01

<400> SEQUENCE: 18

| | |
|---|---|
| tcgaccttca ggtttgtctg taactaaaaa caagtattta agcaaaaaca tcgtagaaat | 60 |
| acggtgtttt ttgttaccct aagtttcagg gcccccctgct tcggggtcat tatagcgatt | 120 |
| ttttcggtat atccatcctt tttcgcacga tatacaggat ttttgccaaag ggttcgtgta | 180 |
| gactttcctt ggtgtatcca acggcgtcag ccgggcagga taggtgaagt aggcccaccc | 240 |
| gcgagcgggt gttccttctt cactgtccct tattcgcacc tggcggtgct caacgggaat | 300 |
| cctgctctgc gaggctggcc ggctaccgcc ggcgtaacag atgagggcaa gcggatggct | 360 |
| gatgaaacca agccaaccag gaagggcagc ccacctatca aggtgtactg ccttccagac | 420 |
| gaacgaagag cgattgagga aaaggcggcg gcggccggca tgagcctgtc ggcctacctg | 480 |
| ctggccgtcg gcagggcta caaaatcacg gcgtcgtgg actatgagca cgtccgcgag | 540 |
| ctggcccgca tcaatggcga cctgggccgc ctgggcggcc tgctgaaact ctggctcacc | 600 |
| gacgacccgc gcacggcgcg gttcggtgat gccacgatcc tcgccctgct ggcgaagatc | 660 |

```
gaagagaagc aggacgagct tggcaaggtc atgatgggcg tggtccgccc gagggcagag    720
ccatgacttt tttagccgct aaaacggccg ggggtgcgc gtgattgcca agcacgtccc     780
catgcgctcc atcaagaaga gcgacttcgc ggagctggtg aagtacatca ccgacgagca    840
aggcaagacc gatcgggccc cctaaacgag tgactcgaga acatgtgagc aaaaggccag    900
caaaaggcca ggaaccgtaa aaaggccgcg ttgctggcgt ttttccatag gctccgcccc    960
cctgacgagc atcacaaaaa tcgacgctca agtcagaggt ggcgaaaccc gacaggacta   1020
taaagatacc aggcgtttcc ccctggaagc tccctcgtgc gctctcctgt tccgaccctg   1080
ccgcttaccg gatacctgtc cgcctttctc ccttcgggaa gcgtggcgct ttctcatagc   1140
tcacgctgta ggtatctcag ttcggtgtag gtcgttcgct ccaagctggg ctgtgtgcac   1200
gaaccccccg ttcagcccga ccgctgcgcc ttatccggta actatcgtct tgagtccaac   1260
ccggtaagac acgacttatc gccactggca gcagccactg gtaacaggat tagcagagcg   1320
aggtatgtag gcggtgctac agagttcttg aagtggtggc ctaactacgg ctacactaga   1380
agaacagtat ttggtatctg cgctctgctg aagccagtta ccttcggaaa aagagttggt   1440
agctcttgat ccggcaaaca aaccaccgct ggtagcggtg gttttttgt ttgcaagcag    1500 cagattacgc gcagaaaaaa aggatctcaa gaagatcctt tgatcttttc tacggggtct   1560
gacgctcagt ggaacgaaaa ctcacgttaa gggattttgg tcatgagatt atcaaaaagg   1620
atcttcacct agatcctttt aaattaaaaa tgaagtttta aatcaatcta agtatatat    1680 gagtaaactt ggtctgacag cctgcaggta atacgactca ctatagggat aacttaaatt   1740 tatattttt actttataat atataattga ttatagaatc caaattagat aggaggacca    1800
ggtaaatgga gaataatttt attgtcaacg aaaacgagaa aagggtttta agcagatat    1860 ttaacaactc caatatcagt agaactcaaa tttccaagaa tttagaactg aataaagcaa   1920
caatttcgaa cattcttaac aatctaaagc ataaaagttt ggtaaatgaa gttggtgaag   1980
gaaattctac taaaagtggt ggaagaaaac ctatacttct cgaaattaat caaaagtatg   2040
ggtattatat aagcatggat ttgacatatg attctgttga gttaatgtat aactattttg   2100
atgctacaat tctcaaacaa gatagttatg aactgaatga taagaatgta agtagcatat   2160
tacagatact caaatctaac ataaatgtta gcgaaaaata cgacacatta tacggtttat   2220
tagggataag tatatccata catgggattg tagatgatga acaaaacatc attaatctac   2280
catttcacaa gaatgaaaaa agaacgttta ctgatgaact taagtctttc actaatgtac   2340
cagtggttat tgaaaatgag gcaaatttaa gtgcattata cgagaaaagt ttatacatca   2400
attcgaatat taacaacttg atcacattgt ctatacataa aggtatagga gctggcatca   2460
taatcaataa gaaactctat agaggtagta atggagaagc tggagaaata ggaaagactc   2520 ttgtttttaga gtctatcaat aacaatgata caagtactaa aaatagag gatatttgta   2580 gtcaagacgc tttgatacaa aagattaata acagattagg agttcactt acatttaccg    2640 aactaataca gtattataac gaaggaaata gtattgtagc tcatgaaatc aaacagttta   2700
tcaacaaaat gactgtctta atacacaatc ttaatactca gtttaatcca gatgcaatat   2760
acatcaattg tcccttgatt aatgaacttc ctaatattct aaacgaaatc aaagaacaat   2820
tctcttgttt ttcacaagga agtcctatac aattgcattt aaccactaat gttaaacaag   2880
ctacattatt aggtggaaca ttagcaatta tgcagaaaac ccttaacata aacaatatcc   2940
aaatgaatat taaatagtta cagcagtctg agttataaaa tagatatctc ggaccgtcta   3000
```

```
ttcttcctta tttgagtggg taccaatgaa atctttcgag ctaaatcgat ttctggccca    3060
ctctttttta tttttttagta agcgtttaca aaaaatgaac aatgtgctat attacctcta    3120
aagttagttt gtttattaaa ttaaccaact aaaatgtcgg gatccaatta ggaggaatct    3180
gcgatggaaa agaaggaatt tagagtttta ataaagtatt gttttcttaa aggaaagaat    3240
acagtagaag ctaagacttg gttagataat gaatttccag attctgctcc tggtaaaagt    3300
acaattatag attggtatgc aaaatttaaa agaggagaaa tgtcaacaga agatggagaa    3360
agatctggta gaccaaaaga agttgtaact gatgaaaata taaagaagat acataaaatg    3420
atattaaatg atagaaagat gaagttaata gaaatagcag aagctttaaa aatatctaaa    3480
gaaagagttg gacatataat acatcaatat ttagatatga gaaaattatg tgcaaaatgg    3540
gttccaagag aattaacttt tgatcaaaag caaagaagag tagatgatag taagagatgt    3600
ttacaattat taacaagaaa tactccagaa tttttcagaa gatatgtaac aatggatgaa    3660
acttggttac atcattatac acctgaaagt aatagacaat cagcagaatg gacagctact    3720
ggagaaccat cacctaaaag aggaaagact caaaagagtg ctggaaaggt tatggcatca    3780
gtattttggg atgctcatgg tataatattt atagattatt tagaaaaagg aaaaacaata    3840
aattctgatt attatatggc attattagaa agattaaaag ttgaaatagc agctaaaaga    3900
ccacatatga gaagaaaaa agtattattt catcaagata atgctccttg tcataagtca    3960
ttaagaacta tggcaaagat acatgaatta ggttttgaat tattaccaca tccaccttat    4020
tcaccagatt tagctccttc tgatttcttt ttatttagtg atttaaagag aatgttagca    4080
ggaaagaagt ttggttgtaa tgaagaagtt atagcagaaa cagaagctta ttttgaagca    4140
aaacctaagg aatattatca aaatggaata aagaagttag aaggtagata taatagatgt    4200
atagcattag aaggaaatta tgtagaataa gaattcctta attaaggagc tcgataaaaa    4260
taagaagcct gcatttgcag gcttcttatt tttatggtca tagctgtttc ctggcgcgcc    4320
gccattattt ttttgaacaa ttgacaattc atttcttatt ttttattaag tgatagtcaa    4380
aaggcataac agtgctgaat agaaagaaat ttacagaaaa gaaaattata gaatttagta    4440
tgattaatta tactcatttta tgaatgttta attgaataca aaaaaaaata cttgttatgt    4500
attcaattac gggttaaaat atagacaagt tgaaaaattt aataaaaaaa taagtcctca    4560
gctcttatat attaagctac caacttagta tataagccaa aacttaaatg tgctaccaac    4620
acatcaagcc gttagagaac tctatctata gcaatatttc aaatgtaccg acatacaaga    4680
gaaacattaa ctatatatat tcaatttatg agattatctt aacagatata aatgtaaatt    4740
gcaataagta agatttagaa gtttatagcc tttgtgtatt ggaagcagta cgcaaaggct    4800
tttttattt ataaaaatta gaagtatatt tatttttca taattaatttt atgaaaatga    4860
aagggggtga gcaaagtgac agaggaaagc agtatcttat caaataacaa ggtattagca    4920
atatcattat tgactttagc agtaaacatt atgactttta tagtgcttgt agctaagtag    4980
tacgaaaggg ggagctttaa aaagctcctt ggaatacata gaattcataa attaatttat    5040
gaaaagaagg gcgtatatga aaacttgtaa aaattgcaaa gagtttatta agatactga    5100
aatatgcaaa atacattcgt tgatgattca tgataaaaca gtagcaacct attgcagtaa    5160
atacaatgag tcaagatgtt tacataaagg gaaagtccaa tgtattaatt gttcaaagat    5220
gaaccgatat ggatggtgtg ccataaaaat gagatgtttt acagaggaag aacagaaaaa    5280
agaacgtaca tgcattaaat attatgcaag gagctttaaa aaagctcatg taagaagag     5340
taaaagaaa aataatttta tttattaatt taatattgag agtgccgaca cagtatgcac    5400
```

```
taaaaaatat atctgtggtg tagtgagccg atacaaaagg atagtcactc gcattttcat    5460
aatacatctt atgttatgat tatgtgtcgg tgggacttca cgacgaaaac ccacaataaa    5520
aaaagagttc ggggtagggt taagcatagt tgaggcaact aaacaatcaa gctaggatat    5580
gcagtagcag accgtaaggt cgttgtttag gtgtgttgta atacatacgc tattaagatg    5640
taaaaatacg gataccaatg aagggaaaag tataattttt ggatgtagtt tgtttgttca    5700
tctatgggca aactacgtcc aaagccgttt ccaaatctgc taaaaagtat atcctttcta    5760
aaatcaaagt caagtatgaa atcataaata aagtttaatt ttgaagttat tatgatatta    5820
tgttttcta ttaaaataaa ttaagtatat agaatagttt aataatagta tatacttaat     5880
gtgataagtg tctgacagtg tcacagaaag gatgattgtt atggattata agcggccggc    5940
cagtgggcaa gttgaaaaat tcacaaaaat gtggtataat atctttgttc attagagcga    6000
taaacttgaa tttgagaggg aacttagatg gtatttgaaa aaattgataa aaatagttgg    6060
aacagaaaag agtattttga ccactacttt gcaagtgtac cttgtaccta cagcatgacc    6120
gttaaagtgg atatcacaca aataaaggaa aagggaatga actatatcc tgcaatgctt     6180
tattatattg caatgattgt aaaccgccat tcagagttta ggacggcaat caatcaagat    6240
ggtgaattgg ggatatatga tgagatgata ccaagctata caatatttca caatgatact    6300
gaaacatttt ccagcctttg gactgagtgt aagtctgact ttaaatcatt tttagcagat    6360
tatgaaagtg atacgcaacg gtatggaaac aatcatagaa tggaaggaaa gccaaatgct    6420
ccggaaaaca tttttaatgt atctatgata ccgtggtcaa ccttcgatgg ctttaatctg    6480
aatttgcaga aaggatatga ttatttgatt cctattttta ctatggggaa atattataaa    6540
gaagataaca aaattatact tcctttggca attcaagttc atcacgcagt atgtgacgga    6600
tttcacattt gccgttttgt aaacgaattg caggaattga taaatagtta acttcaggtt    6660
tgtctgtaac taaaaacaag tatttaagca aaaacatcgt agaaatacgg tgttttttgt    6720
tacccctaagt ttaaacccag agcctacgag ttccgaacta gacaggttgg ctgataagtc    6780
cccggtctgg cgcgacatca taacggttct ggcaaatagt gacttctgaa atgagcataa    6840
aaataagaag cctgcaaatg caggcttctt attttatgg ggaattgtta tccgctcaca     6900
attcccctat agtgagtcgt attaatttcg ccatggtacg taaggcctat ttaaatcacg    6960
tgcggccgca tgtacagcga cgtcactagt ctaagttccc tcctaaaatt caagtttatc    7020
gctctaatga acaaagatat tatactctat caatgataga gtttcaaact ctatcaatga    7080
tagagtgaat ccgttagcga ggttgagtta tcgagatttt caggagcggg tgctagctga    7140
gcccgcggaa cagctgtccc gggagaagtt cctatacttt ctagagaata ggaacttcgg    7200
aataggaact tcttaggta acaaaaaaca ccgtatttct acgatgtttt tgcttaaata    7260
cttgttttta gttacagaca aacctgaagg aattcctaag atccactttc acacttaagc    7320
tgtttctcta gtccgcaaat tattaactcc aatccaaaga gaaacgcagg ttcagctcct    7380
tgatgatcaa acagttctat agcttgtcgt aataaaggtg gcatactatc tgtagtagga    7440
gtttctctct cttctttgc aacttgatgt tcttgatctt ccaaaacaca acctaacgtg     7500
aaatgaccta cagctgaaag agcatataat gcgttctcta atgagaatcc ttgttgacat    7560
agaaatgcca actgattttc aagtgtctca tactgctttt ctgtaggtct agttcctaag    7620
tgaactttag ccccatctct atgggatagt aaagcacatc tgaaacttt cgcgttattc     7680
ctcaaaaagt cttgccaact ttcaccttct aatggacaaa agtgtgtatg atgtctgtct    7740
```

```
aacatttcga ttgctaatgc atctaagagt gctcttttgt ttttgacatg ccagtacaat    7800
gttggttgtt caactccaag tttctgagct aatttcctgg tagttagacc ttcaattcca    7860
acttcattaa ggagttctaa tgcggaattt atcactttag acttatcgag tctactcatt    7920
ctaactaacc tcctaacaac ttaattatac ccactattat tattttatc aatatatgcc     7980 tgcagcgacc aaaagtataa aacctttaag aactttcttt tttcttgtaa aaaagaaac     8040 tagataaatc tctcatatct tttattcaat aatcgcatca gattgcagta taaatttaac    8100
gatcactcat catgttcata tttatcagag ctcgtgctat aattatacta attttataag    8160
gaggaaaaaa taaagagggt tataatgaac gagaaaaata taaaacacag tcaaaacttt    8220
attacttcaa aacataatat agataaaata atgacaaata taagattaaa tgaacatgat    8280
aatatctttg aaatcggctc aggaaaaggg catttacccc ttgaattagt acagaggtgt    8340
aatttcgtaa ctgccattga aatagaccat aaattatgca aaactacaga aataaactt     8400 gttgatcacg ataatttcca agttttaaac aaggatatat tgcagtttaa atttcctaaa    8460
aaccaatcct ataaaatatt tggtaatata ccttataaca taagtacgga tataatacgc    8520
aaaattgttt ttgatagtat agctgatgag atttatttaa tcgtggaata cgggtttgct    8580
aaaagattat taaatacaaa acgctcattg gcattatttt taatggcaga agttgatatt    8640
tctatattaa gtatggttcc aagagaatat tttcatccta aacctaaagt gaatagctca    8700
cttatcagat taaatagaaa aaaatcaaga atatcacaca aagataaaca gaagtataat    8760
tatttcgtta tgaaatgggt taacaaagaa tacaagaaaa tatttacaaa aaatcaattt    8820
aacaattcct taaaacatgc aggaattgac gatttaaaca atattagctt tgaacaattc    8880
ttatctcttt tcaatagcta taaattattt aataagtaag ttaagggatg cataaactgc    8940
atcccttaac ttgttttttcg tgtacctatt ttttgtgaat cgattatgtc ttttgcgcat    9000
tcacttcttt tctatataaa tatgagcgaa gcgaataagc gtcggaaaag cagcaaaaag    9060 tttcctttt gctgttggag catggggggt caggggggtgc agtatcgaag ttcctatact    9120
ttctagagaa taggaacttc ggaataggaa cttcccggga atgtagaccg gggacttatc    9180
agccaacctg ttagatggcc cgcacgatca aggcgcgcca ggaaacagct atgaccg       9237
```

<210> SEQ ID NO 19
<211> LENGTH: 2545
<212> TYPE: DNA
<213> ORGANISM: Artificial
<220> FEATURE:
<223> OTHER INFORMATION: Expression vector pSCi::idi-isps

<400> SEQUENCE: 19

```
atgacagcag ataacaattc tatgccacat ggagcagttt caagttatgc gaaattagtt     60
cagaaccaaa ctccagaaga catactagag gaatttccag aaatcatacc cttacaacaa    120
agaccaaata caagaagttc ggaaacatct aatgatgaat caggtgaaac ttgttttttca    180 ggacatgatg aagaacagat caaactcatg aacgagaatt gtattgttct tgattgggac    240
gataatgcta taggtgctgg tactaaaaag gtttgtcact taatggaaaa tatcgaaaag    300
ggattgttac acagagcatt tagtgtattt atctttaatg aacaaggaga attactactt    360
caacaaagag ctacagaaaa gataacgttt cctgatttat ggaccaatac ttgttgtagt    420
catcctctat gtatagatga tgagttagga cttaaaggca aattgacga caaaatcaaa    480 ggtgctataa cagcagctgt aagaaagtta gatcatgagt taggaatacc tgaagatgag    540
actaaaacta gaggaaaatt ccatttctt aaccgtatcc attatatggc accttctaat    600
```

```
gaaccttggg gtgaacatga aatcgattat atcttgttct acaaaatcaa tgctaaggaa      660
aatcttactg tgaatcccaa tgtaaatgaa gtaagagatt ttaagtgggt tagtcctaat      720
gatctgaaaa ccatgtttgc agatccttcc tataaattta caccttggtt taagattata     780
tgcgagaatt atctctttaa ttggtgggaa caattggatg atttgagtga agttgagaat      840
gacagacaaa tacatcgaat gttatagtag tgataccgtt taaacaggaa gaatcataga     900
ggaggaatca atggaagcga acgcagtgc caattatgaa ccaaatagct gggattatga      960
ttatcttctg agtagtgata ccgatgaaag cattgaagta tataaagata aagccaaaaa     1020
attagaagca gaagtgagac gtgaaattaa taatgaaaaa gctgaatttc tgacactgtt     1080
agaacttatt gataatgtgc agcgcctggg attaggctat agatttgaaa gcgatattag     1140
aggcgcactg gatcgttttg tgagttcagg tggatttgat gctgttacaa aaactagcct     1200
tcatggaact gcgctgagtt ttcgccttct gagacagcac ggctttgaag ttagccaaga     1260
agcctttagt ggttttaaag atcaaaatgg aaattttctg gaaaatctta agaagatat      1320 taaagcaata ctttcactgt atgaagcaag ttttctggca cttgaaggag aaaatatact     1380
tgatgaagct aaagttttg cgatttcaca tcttaaagaa ctgtctgaag aaaaaattgg     1440
caaagaactg gctgaacagg ttaatcatgc gctggaatta ccgcttcacc gcagaaccca     1500
aagattagaa gccgtttggt ctattgaagc atatcgtaaa aaagaagatg ccaatcaggt     1560
acttcttgaa ttagcaatac ttgattataa tatgattcag agcgtgtatc aacgtgatct     1620
tcgcgaaacc agtagatggt ggcgtcgcgt tggccttgct acgaaactgc attttgcgag     1680
agatcgtctg attgaaagct tttattgggc cgtgggtgtt gcatttgaac cacaatatag     1740
cgattgtcgt aatagtgttg caaaaatgtt tagttttgta actataattg atgatattta     1800
tgatgtttat ggtacacttg atgaactgga acttttttact gatgctgtag aacgctggga     1860
tgtgaatgcg attaatgatc tgccagatta tatgaaactt tgttttcttg ccctgtataa     1920
tacaattaat gaaattgcat atgataatct taaagataaa ggagaaaata tactgcctta     1980
tttaactaaa gcatgggctg atttatgcaa tgcttttctt caggaagcga atggctgta      2040 taataaatca accctacgt tgatgatta ttttggcaat gcttggaaat ctagcagtgg       2100
tccgttacag cttgttttg cttatttgc ggttgtacaa aatattaaaa aagaagaaat      2160
tgaaaatctg caaaaatatc atgatactat ttcacgtcct tctcacatat ttcgcttatg     2220
taatgatctt gcgtcagcaa gtgcagaaat tgcccgcggt gaaaccgcaa atagcgtaag     2280
ttgctatatg agaacaaaag gaatttcaga agaacttgca actgaatctg tgatgaatct     2340
gattgatgaa acctggaaga aaatgaataa agaaaaatta ggcggttctc tgtttgctaa     2400
accatttgta gaaacggcta taaatcttgc gcgtcagtca cattgcacct atcacaatgg     2460
agatgcgcat acgtctccgg atgaacttac cagaaaaaga gtgctgagtg tgattaccga     2520
accgatactg ccatttgaac gctaa                                            2545

<210> SEQ ID NO 20
<211> LENGTH: 9818
<212> TYPE: DNA
<213> ORGANISM: Artificial
<220> FEATURE:
<223> OTHER INFORMATION: Isoprene synthase gene cluster

<400> SEQUENCE: 20
atttaaatac tatcaagaga agaataaaga aggaggttta aaaatgaaaa attgtgtaat      60
```

-continued

```
tgtgagtgct gtaagaacag caataggaag ctttaatgga tcattggcta gtacatctgc    120
aattgatctt ggtgcaactg taataaaggc tgctattgaa agagcaaaaa ttgattcaca    180
acatgttgac gaagtaataa tgggaaacgt attacaagca ggacttggac aaaatccagc    240
aagacaggca cttttgaaaa gtggattagc tgaaactgta tgtggattca ctgttaataa    300
ggtttgtggt tctggactta aatctgtagc acttgcagct caagctatac aagctggaca    360
agctcagtca atagttgctg gtggcatgga aaatatgtca ttggcacctt atcttcttga    420
tgcaaaagca agatcaggat atagattggg tgatggacaa gtgtatgatg taatattaag    480
agacggatta atgtgcgcaa ctcatggata ccatatgggt ataacagctg aaaatgtagc    540
aaaagagtat ggaataacaa gagagatgca agatgagtta gctcttcatt ctcagagaaa    600
agctgctgct gctattgaat ctggtgcttt tactgcagaa atagtaccag ttaatgtagt    660
gactaggaaa aagactttg tttttagcca agatgaattt cctaaagcaa acagtacagc    720
agaagcatta ggcgcattaa ggcctgcttt tgataaagct ggtacagtta cagctggaaa    780
tgctagtgga attaatgacg gtgctgctgc attggttata atggaagaaa gtgctgcttt    840
agctgcagga cttactcctt tagcaaggat taaaagctat gcatctggtg gcgtaccacc    900
agcattaatg ggtatgggtc ctgttccagc aacacagaag gcattgcaat tagcaggatt    960
acagttagct gatattgatt tgattgaggc aaatgaagct tttgctgctc agttttttagc   1020
agtaggtaag aatcttggat ttgatagtga aaaagtaaac gttaatggtg gcgcaatagc   1080
acttggacat cctattggtg catcaggtgc tagaatactt gtgacattat tacacgctat   1140
gcaagctaga gataaaactt taggtcttgc aactttatgt attggcggtg gccagggtat   1200
agcaatggtt atagaaagat taaattaagg atcccaataa acagggatta acatataggaa   1260
ggtaaaataa tgacaatagg catagacaaa atatcatttt tcgtacctcc ttattatata   1320
gatatgactg cattagctga ggcaagaaat gttgatcctg gtaaattcca cattggaata   1380
ggacaagatc aaatggcagt taatccaatt tctcaagata tagttacatt tgctgctaac   1440
gcagctgagg caattcttac taaagaagac aaagaagcaa ttgatatggt aatagtaggt   1500
actgaatcta gtatagatga gtctaaggct gcagctgttg ttttacacag attaatgggt   1560
attcaacctt tgctagaag cttttgaaatt aaagaagctt gttatggcgc tacagcaggt   1620
cttcaattgg ctaaaaatca tgtagctctt catcctgata agaaagtatt agtagtggca   1680
gcagacatag caaaatatgg attgaattct ggtggtgaac tactcaagg cgctggtgca   1740
gtagcaatgt tagtggcatc agaacctaga attcttgctt taaaagaaga taacgttatg   1800
ttgactcagg acatatatga tttttggaga ccaacaggtc atccatatcc aatggttgat   1860
ggaccattga gtaatgagac ttatattcag agctttgctc aagtttggga tgagcataag   1920
aaaagaacag gacttgattt tgctgattac gatgcattag catttcatat tccatacact   1980
aaaatgggta aaaggctttt attagcaaag ataagtgacc aaactgaggc agaacaagaa   2040
agaatatttag ctaggtacga agaaagtatt atttattcaa gaagagttgg aaatttatac   2100
actggtagcc tttatttggg tttaatatct ttacttgaga atgctacaac acttacagct   2160
ggtaatcaaa taggattgtt tagttatggc tctggtgcag tagcagaatt tttcactggc   2220
gaacttgtag caggatatca gaatcactta caaaagaaa ctcatttagc attacttgac   2280
aatagaacag agcttagtat tgcagaatat gaggctatgt ttgctgagac acttgataca   2340
gatatagatc agacacttga agacgaattg aaatactcaa tatcagctat aaacaatact   2400
gtaaggtcat atagaaatta accatggtgg aatacaatag agacatataa ggaggacaaa   2460
```

```
aaatggttgc agattcaaga ttacctaatt ttagagctct tacaccagct cagagaagag   2520
atttcttagc tgatgcatgt ggattgtcag atgcagaaag gcattactt gctgctcctg    2580 gtgctttacc attagcatta gcagacggta tgattgaaaa tgttttgga tcttttgaat    2640 taccacttgg cgttgctgga aattttagag ttaacgaag agatgttctt gttccaatgg    2700
ctgtagaaga accttcagtg gtagcagcag catcttatat ggctaagctt gcaagagaag   2760
acggcggttt tcaaacttct tctactttac ctttaatgag agcacaggta caagtattag   2820
gtgtgacaga tcctcatggc gctaggttag cagttcttca agctagagct caaataatag   2880
aaagggcaaa ttcaagagat aaagttttaa taggacttgg tggtggctgc aaagatatag   2940
aagtacacgt atttccagat actcctagag gtcctatgct tgtagttcat ttaatagttg   3000
acgtaagaga cgctatgggt gctaatacag ttaatacaat ggctgaaagt gttgcacctt   3060
tagtggaaaa gattactggc ggtagtgtaa gattaagaat tctttcaaat cttgcagatc   3120
ttagattagc tagggctaga gtaagattga caccacagac attggctaca caagatagaa   3180
gtggtgaaga gataatagaa ggtgtacttg acgcatatac atttgctgct attgatccat   3240
atagggctgc tactcataat aaaggtataa tgaacggtat tgatccagtt attgtagcta   3300
ctggaaacga ttggagagca gtggaagcag gtgcacatgc ttatgcaagt agaagcggaa   3360
gttacactag cttgactaga tgggaaaaag atgctggcgg tgctcttgta ggatctatag   3420
aacttccaat gccagtagga cttgtgggtg gtgcaactaa aactcatcct ttggcaaggt   3480
tggcacttaa aataatggat ttgcaaagtg cacaacaact tggtgagata gctgctgcag   3540
ttggattggc acagaatctt ggtgcattaa gggctttagc aactgaaggt atacaaagag   3600
gccatatggc tttgcacgct agaaatattg ctttagtagc tggtgctaca ggtgatgaag   3660
ttgatgctgt tgctaggcag cttgctgctg aacatgacgt tagaacagat agggcacttg   3720
aagttttagc tgcacttaga gcaagagctt aagttcaaac actatcataa cacacaatag   3780
aaaggaggat aaaaatggt tcatgtagc gcaccaggta agatatattt atttggtgaa    3840
catgctgtag tatatggcga aacagctata gcatgcgctg tagaattaag gactagggta   3900
agagcagaac ttaacgattc aataacaata caatcacaga ttggtagaac aggacttgat   3960
tttgaaaagc acccatatgt atctgctgta attgaaaaga tgagaaaatc aatacctata   4020
aatggtgtat tcttgactgt tgatagtgac ataccgttg gatctggact tggatcttca    4080
gcagcagtta ctattgcttc tattggtgct ttgaatgagt tatttggttt tggacttagt   4140
cttcaagaga tagctaaaatt aggacatgaa attgaaatta aagttcaggg tgcagctagt   4200
ccaacagaca catatgtaag cacttttggc ggtgtagtta caattccaga aagaagaaaa   4260
cttaaaacac cagattgtgg aatagtgatt ggtgatacag gcgttttag ttcaactaaa   4320 gagttagtgg ctaatgtaag acagttaaga gaatcttatc ctgatcttat tgagccattg   4380
atgacttcaa taggaaaaat aagcaggatt ggtgaacaac ttgttttaag tggtgattac   4440
gcatctatag gtagattaat gaatgtgaat cagggacttt tggatgcatt aggtgtaaat   4500
atattggaac ttagccaact tatttatagt gcaagagcag ctggtgcttt tggcgcaaag   4560
ataactggtc tggtggtgg cggttgtatg gttgcattaa ctgcacctga gaaatgtaac   4620
caagtagcag aagctgttgc aggtgctggc ggtaaggtta caataactaa gcctactgaa   4680
cagggattaa aagtagatta agcgccattc gatggtgtcc gtccagataa aaataagaag   4740
cctgcatttg caggcttctt attttttatga gcgaagcgaa taagcgtcgg aaaagcagac   4800
```

```
tctatcattg atagagtttg aaactctatc attgatagag tataatatct tgtttaaacg    4860
gtaccgaagt actaacaagt caaattaagg agggaaaaat atggaagcaa gaagatcagc    4920
aaattacgag ccaaatagtt gggattatga ctatctttta tcttcagata cagatgaatc    4980
tatagaagta tataaggata aagcaaagaa attggaagca gaagtaagaa gagagataaa    5040
taatgaaaag gcagaatttt taactcttct tgaacttata gataatgtgc aaaggcttgg    5100
attaggatat agatttgaat cagatattag aggcgcatta gatagatttg tatctagtgg    5160
cggttttgat gctgttacaa aaacatcact tcatggaaca gctcttagtt tcagattatt    5220
aaggcaacat ggatttgaag tttctcaaga agcttttttct ggatttaaag accaaaatgg    5280
aaatttcctt gaaaatctta agaagatat aaaggcaatt ttatctttat atgaagcatc    5340
atttttggca ttagaaggtg aaaacatatt agatgaggca aaagttttg ctataagtca    5400 tcttaaagaa ctttctgaag aaaagatagg aaaagagtta gcagagcaag taaatcatgc    5460
tcttgaatta cctttacaca gaagaacaca aagattagaa gcagtgtggt ctattgaagc    5520
atacagaaag aaagaagatg ctaatcaggt attattagaa ttggcaattt tagattataa    5580
tatgatacag tctgtgtatc aaagggattt aagagagact agtagatggt ggagaagagt    5640
aggattggct acaaaattgc attttgctag agacagactt attgaatcat tttattgggc    5700
tgttggtgta gcttttgaac ctcagtatag cgattgtaga aacagtgtag caaaaatgtt    5760
cagttttgta actataatag atgacattta tgatgtatat ggaactcttg atgaattgga    5820 acttttttaca gacgcagtag aaagatggga tgtgaatgca ataaatgact tacctgatta    5880
tatgaaatta tgctttcttg cattatacaa tactattaat gagattgcat atgataattt    5940
gaaagataaa ggtgaaaata ttcttcctta tttaactaaa gcttgggctg atttatgcaa    6000
cgcattctta caagaagcta atggttgta taataaatca acaccaacat ttgatgatta    6060
ttttggtaac gcttggaaat ctagctcagg accattgcag ttagtttttg cttatttttgc    6120 tgttgttcag aatataaaga aagaagaaat agagaactta caaaaatatc atgatactat    6180
atcaaggcca agtcatattt ttaggctttg taatgactta gcatctgctt ctgctgaaat    6240
tgctagaggc gaaactgcaa attcagttag ttgttacatg agaacaaagg gtataagtga    6300
agaattagca actgagagcg taatgaactt aatagatgaa acttggaaaa agatgaataa    6360
agagaaactt ggcggtagtc tttttgctaa accatttgta gagactgcaa taaatttggc    6420
aaggcaatca cattgtacat atcataatgg tgatgctcac actagccctg atgagttaac    6480
tagaaagaga gttcttagtg ttattacaga accaatattg ccttttgaaa ggtaagcatg    6540
ctctagaata gacaaatcga catttaaaaa ggaggacaat atatgataga agtaacaaca    6600
ccaggtaaat tatttatagc aggtgaatac gcagtagttg aacctggaca ccctgctata    6660
atagtagctg ttgatcagtt tgttacagta acagttgaag agacaacaga tgaaggatca    6720
atacagtctg ctcaatatag ctcattgcca attagatgga caagaagaaa tggtgagtta    6780
gttttggata taagagaaaa tccatttcat tatgttcttg cagcaataca tttgactgag    6840
aaatacgctc aagaacaaaa taaagaactt tcttttttatc atcttaaggt tacttctgaa    6900
ttggattctt caaatggtag aaaatacgga ttaggaagct caggtgctgt aactgtaggt    6960
acagtaaaag cattaaatat attctatgac ttaggattag aaaatgaaga aattttttaag    7020 ctttctgcac ttgctcattt agcagtgcaa ggtaatggat catgtggtga tattgctgca    7080
agttgttatg gtggctggat agcattcagt acttttgatc atgattgggt aaaccaaaag    7140
gtagcaactg aaacacttac agatttgctt gcaatggatt ggccagagtt aatgattttt    7200
```

```
cctcttaaag tgccaaaaca attaagatta ttaattggct ggactggtag tcctgcaagt    7260
acaagcgact tagttgatag agttcatcag tctaaagaag aaaagcaagc agcttatgag    7320
caatttctta tgaaaagtag gttatgcgtg gaaacaatga ttaatggatt taatactgga    7380
aaaattagtg tgatacagaa acagataact aaaaacagac aacttcttgc tgagttatct    7440
tctttaactg gtgtagtaat tgaaactgaa gcattgaaaa acttatgcga tttagcagag    7500
tcatatactg gtgctgcaaa atcatcaggt gctggtggtg gcgattgtgg aatagttata    7560
tttagacaaa agagtggcat tttgcctctt atgactgctt gggaaaaaga cggaattaca    7620
cctcttccac ttcatgttta tacatatgga cagaaagaat gtaaagagaa gcacgaaagt    7680
aaaaggtaag tcgagaaaaa ctaaaggtac taataaaagg aggttaaaag atgttatctg    7740
gaaaagcaag ggcacacaca aatatagctc ttataaaata ttggggtaag gctaatgaag    7800
aatatatatt accaatgaac agttcacttt ctttaacatt agatgcattc tatactgaaa    7860
caactgtgat atttgacgca cattattcag aagatgtttt tatattagat ggtatacttc    7920
aaaatgaaaa acagactaaa aaggtaaaag agttttttaaa cttagtaagg cagcaagctg    7980
attgtacttg gtttgctaaa gttgaaagtc aaaattttgt gcctacagct gctggattgg    8040
cttcaagtgc aagcggattg gcagcattag caggtgcatg taacgtagct ttaggactta    8100
atttaagcgc taaggatctt tcaagattag caagaagagg ctctggatca gcttgtagaa    8160 gtattttttgg cggttttgct caatggaata agggacatag cgatgaaaca tcttttgctg    8220
aaaacattcc agcaaataat tgggaaaatg aattagctat gcttttcata ttgattaatg    8280
atggtgaaaa ggatgtttct agtagagatg gtatgaaaag aactgttgag acaagtagtt    8340
tttatcaggg ttggcttgac aatgtagaaa aggatctttc acaggttcat gaagctatta    8400
aaacaaaaga ttttcctagg ttaggtgaaa ttattgaggc aaatggattg agaatgcatg    8460
gtactacatt gggtgctgtt cctccattta catactggtc acctggatct ttgcaagcta    8520
tggcattagt tagacaggct agagcaaagg gtataccttg ctacttcact atggatgcag    8580
gaccaaatgt aaaagtactt gtagagaaga aaaatttgga agcattaaag acttttctta    8640
gcgaacattt ttctaaagaa caacttgtgc ctgcttttgc aggtccaggt attgagtat    8700 ttgaaactaa aggcatggac aaataagagc tcgacaataa acacaggtaa gtaaaggagg    8760
ttaagaaatg caaacagaac acgtaatatt attaaacgca caaggtgttc ctactggaac    8820
acttgaaaag tatgctgcac atacagctga tacaagactt catttagctt tttcttcatg    8880
gttattcaat gctaaaggac aacttcttgt aactagaaga gcactttcta agaaagcttg    8940
gcctggtgtt tggactaaca gtgtttgtgg acatcctcag ttaggtgaaa gtaatgaaga    9000
tgcagtaatt agaaggtgca gatacgaatt aggtgtagaa ataactcctc ctgagagtat    9060
atatcctgat tttaggtata gagcaactga tccatctggc atagtagaga atgaagtatg    9120
tccagtgttt gcagcaagaa ctacatcagc attgcaaatt aatgatgatg aagtaatgga    9180
ctatcagtgg tgtgacttag cagatgtttt acatggaatt gacgcaactc catgggcttt    9240
tagcccatgg atggtgatgc aagctacaaa tagagaagct agaaaaagat tgtcagcttt    9300
tacacagttg aaataagcta gctgttcaaa acaatcgcaa attaaggagg ctaataaatg    9360
ataaacgcaa aacttttaca acttatggta gaacattcaa acgatggaat tgttgtagct    9420
gaacaagaag gtaatgaaag catattgatt tatgttaatc ctgcatttga aaggttaaca    9480
ggttattgtg cagacgatat attatatcaa gatgcaaggt ttcttcaagg tgaagatcac    9540
```

```
gatcagcctg gaattgctat tataagagaa gctattagag aaggcagacc atgctgtcag      9600
gttttaagaa attatagaaa agacggatct ttattttgga atgagcttag tataactcca      9660
gtgcataatg aggctgatca attaacttat tacataggta tacaaagaga tgtaacagct      9720
caagttttcg ctgaagaaag agtgagagaa ttggaagcag aagtagcaga gcttagaaga      9780
caacagggac aggcaaagca ttaagtccag atttaaat                              9818
```